US009642875B2

(12) United States Patent
Frost et al.

(10) Patent No.: US 9,642,875 B2
(45) Date of Patent: May 9, 2017

(54) COMPOUNDS AND THEIR EFFECTS ON APPETITE CONTROL AND INSULIN SENSITIVITY

(71) Applicants: Imperial Innovations Limited, Greater London (GB); The University Court of the University of Glasgow, Glasgow (GB)

(72) Inventors: Gary Frost, Greater London (GB); Douglas Morrison, Glasgow (GB); Thomas Preston, Glasgow (GB)

(73) Assignees: The University Court of the University of Glasgow, Glasgow (GB); Imperial Innovations Limited, Greater London (GB)

( * ) Notice: Subject to any disclaimer, the term of this patent is extended or adjusted under 35 U.S.C. 154(b) by 0 days.

(21) Appl. No.: 14/418,448

(22) PCT Filed: Jul. 31, 2013

(86) PCT No.: PCT/GB2013/052056
§ 371 (c)(1),
(2) Date: Jan. 30, 2015

(87) PCT Pub. No.: WO2014/020344
PCT Pub. Date: Feb. 6, 2014

(65) Prior Publication Data
US 2015/0196583 A1   Jul. 16, 2015

(30) Foreign Application Priority Data

Jul. 31, 2012 (GB) .................................. 1213629.7

(51) Int. Cl.
*A23L 1/30* (2006.01)
*A61K 31/733* (2006.01)
*A61K 45/06* (2006.01)
*C08B 37/00* (2006.01)
*C08L 5/00* (2006.01)
*A61K 49/12* (2006.01)
*A23L 33/10* (2016.01)
*A23L 33/21* (2016.01)

(52) U.S. Cl.
CPC ............ *A61K 31/733* (2013.01); *A23L 33/10* (2016.08); *A23L 33/21* (2016.08); *A61K 45/06* (2013.01); *A61K 49/126* (2013.01); *C08B 37/0054* (2013.01); *C08L 5/00* (2013.01); *A23V 2002/00* (2013.01)

(58) Field of Classification Search
None
See application file for complete search history.

(56) References Cited

U.S. PATENT DOCUMENTS

| 5,840,860 | A | * | 11/1998 | Annison | ............... | A21D 2/16 |
| | | | | | | 436/71 |
| 5,877,144 | A | * | 3/1999 | Ehrhardt | ............... | A61K 8/73 |
| | | | | | | 510/130 |
| 6,525,095 | B1 | | 2/2003 | Petersen et al. | | |
| 2003/0203004 | A1 | | 10/2003 | Kelm et al. | | |
| 2008/0213341 | A1 | | 9/2008 | Haji Begli et al. | | |
| 2009/0123388 | A1 | | 5/2009 | Ganapathy et al. | | |

FOREIGN PATENT DOCUMENTS

| EP | 0898900 A2 | 3/1999 | |
| KR | 20090030441 A | 3/2009 | |
| NL | WO 0100771 A1 * | 1/2001 | ......... C08B 37/0051 |
| WO | 9901149 A1 | 1/1999 | |
| WO | 0202102 A1 | 1/2002 | |
| WO | 03090557 A1 | 11/2003 | |

OTHER PUBLICATIONS

Ford, Proceedings of the Nutrition Society (2010), 69, 199-203.*
International Search Report and Written Opinion issued in corresponding International Patent Application No. PCT/GB2013/052056 dated Oct. 9, 2013 (14 pages).
Al-Lahham et al., "Biological effects of propionic acid in humans; metabolism, potential applications and underlying mechanisms," Biochimica et Biophysica Acta, 2010, vol. 1801, pp. 1175-1183.
Arora et al., "Propionate. Anti-obesity and satiety enhancing factor?," Appetite, vol. 56, No. 2, 2011, pp. 511-515.
Berggren et al., "Influence of orally and rectally administered propionate on cholesterol and glucose metabolism in obese rats," British Journal of Nutrition, vol. 76, No. 2, 1996, pp. 287-294.
Darzi et al., Conference on 'Nutrition and health: cell to community,' Postgraduate Symposium, "Do SCFA have a role in appetite regulation?," Proceedings of the Nutrition Society, 2011, vol. 70, pp. 119-128.
Database WPI, Week 200927, AN 2009-H17471, XP002713756, Thomson Scientific (2 pages).
Djouzi et al., "Compared effects of three oligosaccharides on metabolism of intestinal microflora in rats inoculated with a human faecal flora," British Journal of Nutrition, vol. 78, 1997, pp. 313-324.
Farningham et al., "The role of propionate and acetate in the control of food intake in sheep," British Journal of Nutrition, vol. 70, No. 1, 1993, pp. 37-46.
Hughes et al., "In vitro fermentation of oat and barley derived beta-glucans by human faecal microbiota," FEMS Microbiol. Ecol., vol. 64, 2008, pp. 482-493.
Kuhn et al., "Purification of fructooligosaccharides in an activated charcoal fixed bed column," New Biotechnology, vol. 27, No. 6, 2010, pp. 862-869.

(Continued)

*Primary Examiner* — Layla Berry
(74) *Attorney, Agent, or Firm* — Kilyk & Bowersox, P.L.L.C.

(57) ABSTRACT

The invention provides a propionate inulin ester for the reduction of appetite, food intake and/or calorie intake and/or to improve insulin sensitivity in a subject, and for the treatment or prevention of obesity or diabetes. The invention also provides compositions comprising a propionate inulin ester, methods using propionate inulin esters, functional food containing propionate inulin ester and methods of making propionate inulin esters.

22 Claims, 23 Drawing Sheets

(56) References Cited

OTHER PUBLICATIONS

Lin et al., "Butyrate and Propionate Protect against Diet Induced Obesity and Regulate Gut Hormones via Free Fatty Acid Receptor 3-Independent Mechanisms," PLoS One, vol. 7, No. 4, 2012, pp. 1-9.
Mortensen et al., Short-Chain Fatty Acid Production from Mono- and Disaccharides in a Fecal Incubation System: Implications for Colonic Fermentation of Dietary Fiber in Humans, J Nutr., vol. 188, 1988, pp. 321-325.
Polyviou et al., "Randomised clinical study: inulin short-chain fatty acid esters for targeted delivery of short-chain fatty acids to the human colon," Alimentary Pharmacology and Therapeutics, doi:10.1111/apt.3749, 2016, pp. 1-11.
Tarini et al., "The fermentable fibre inulin increases postprandial serum short-chain fatty acids and reduces free-fatty acids and ghrelin in healthy subjects," Applied Physiology, Nutrition and Metabolism, vol. 35, No. 1, 2010, pp. 9-16.
Tolhurst et al., "Short-Chain Fatty Acids Stimulate Glucagon-Like Peptide-1 Secretion via the G-Protein—Coupled Receptor FFAR2," Diabetes, vol. 61, 2012, pp. 364-371.
Vince et al., "The effect of lactulose, pectin arabinogalactan and cellulose on the production of organic acids and metabolism of ammonia by intestinal bacteria in a faecal incubation system," British Journal of Nutrition, vol. 63, 1990, pp. 17-26.
Vogt et al., "L-Rhamnose increases serum propionate in humans," American Journal for Clinical Nutrition, vol. 80, 2004, pp. 89-94.

* cited by examiner

* = p < 0.05

Figure 4
A
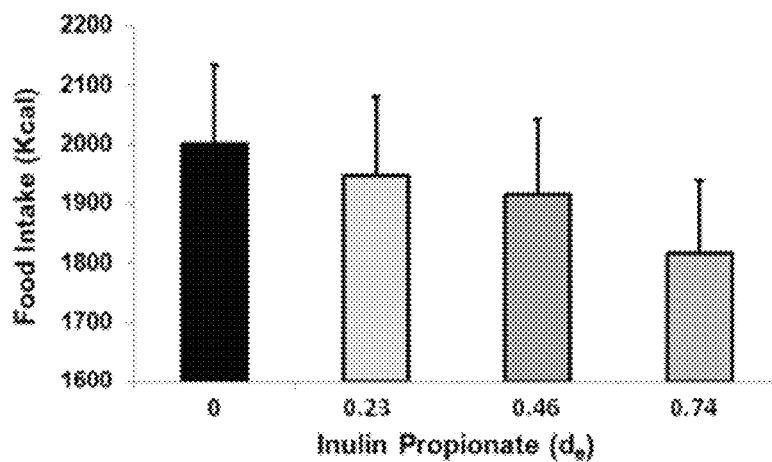
B
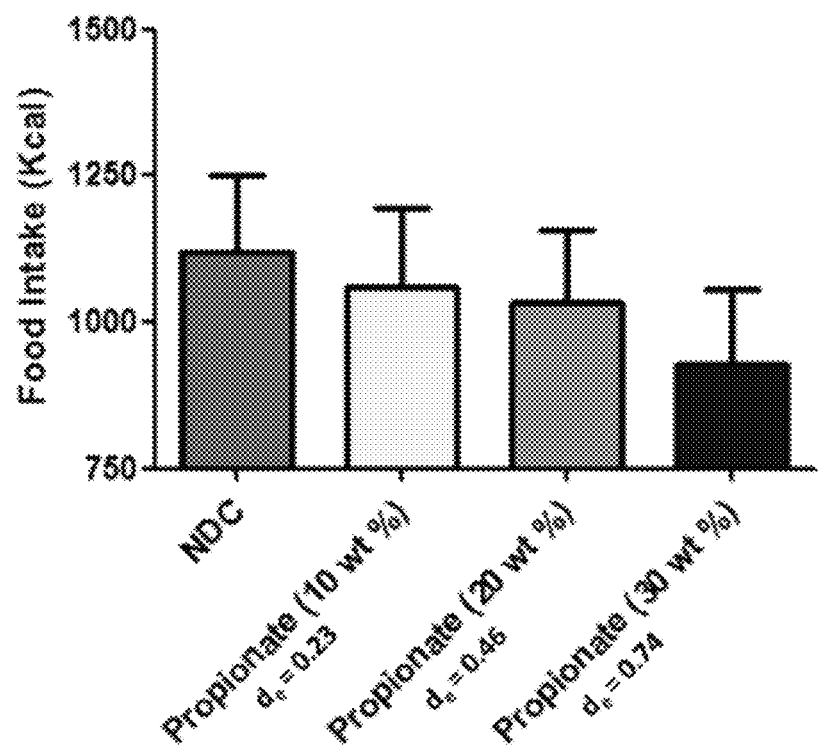

* = p < 0.05

Figure 7
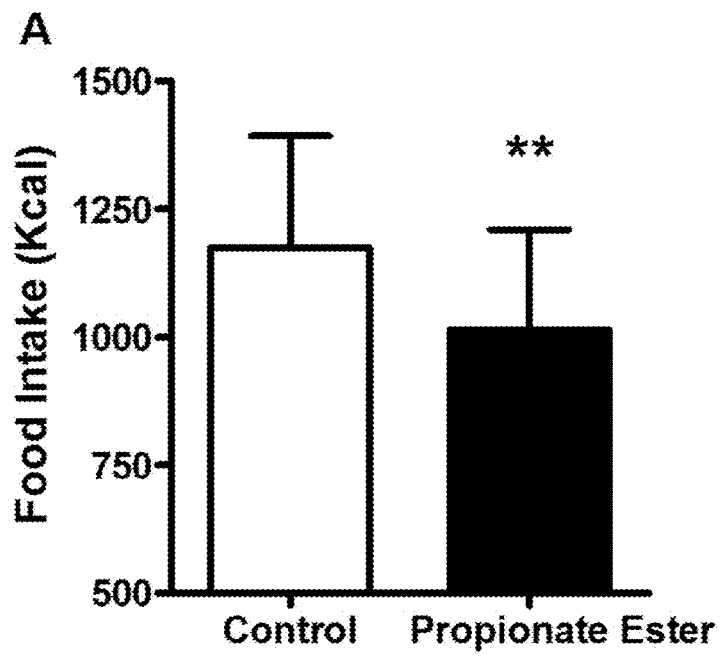
** = p > 0.05
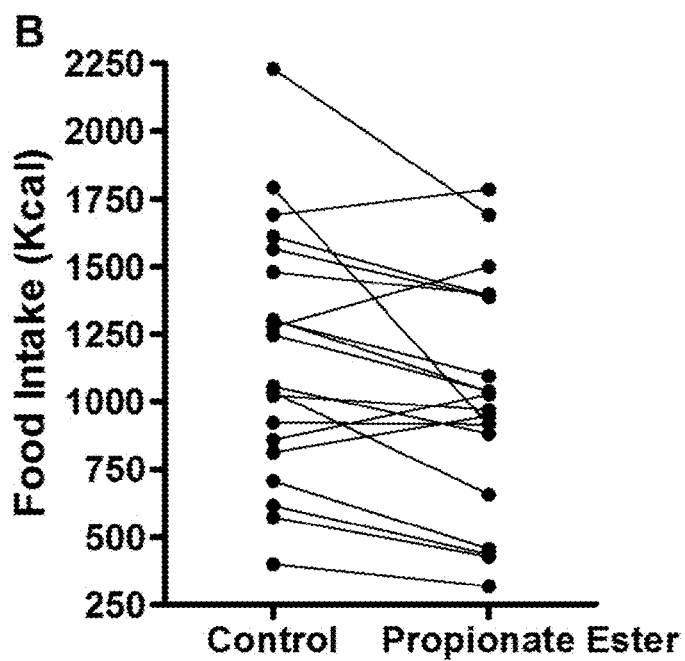

Figure 8
a) How hungry do you feel right now?
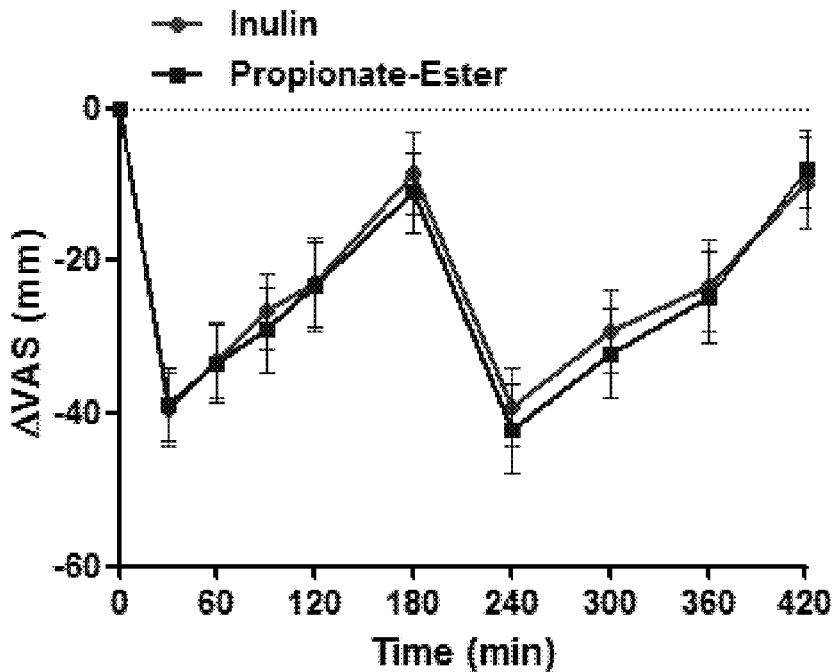
b) How sick do you feel right now?
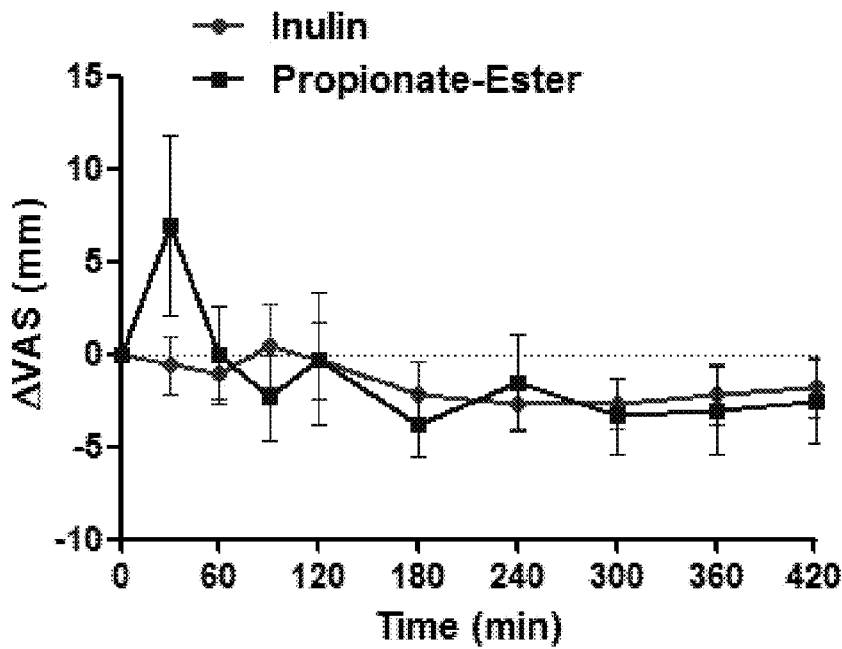

Figure 8 cont'd
c) How pleasant would it be to eat right now?
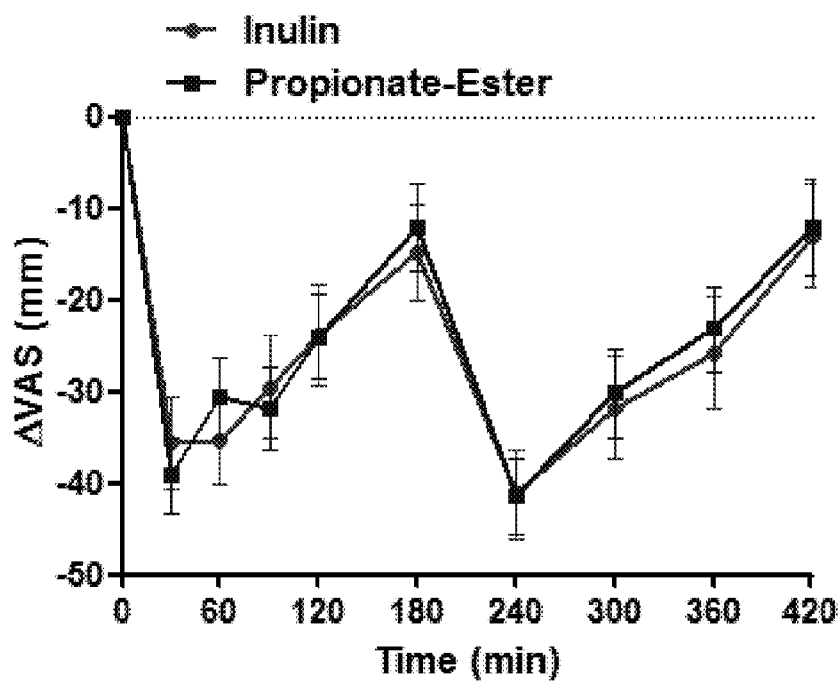
d) How much do you think you could eat right now?
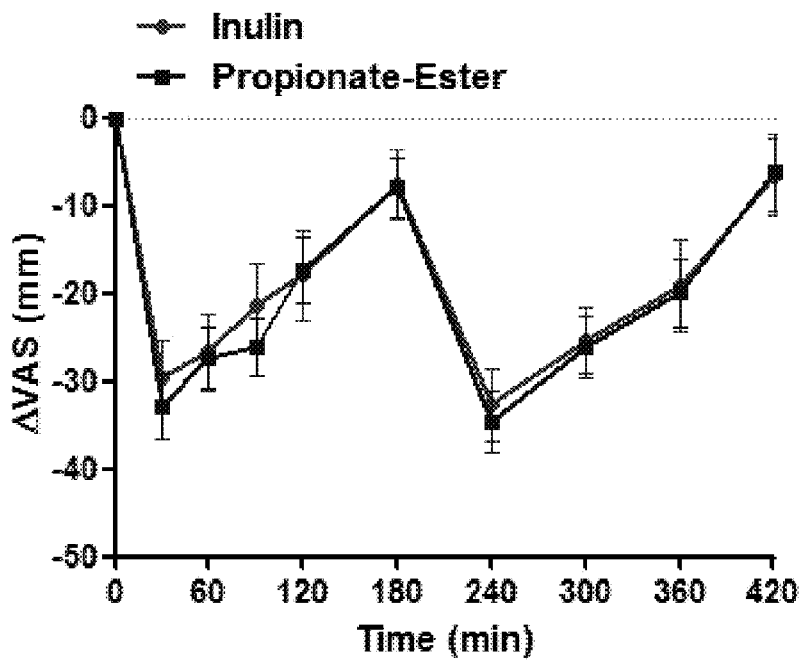

e) How full do you feel right now?

Figure 9
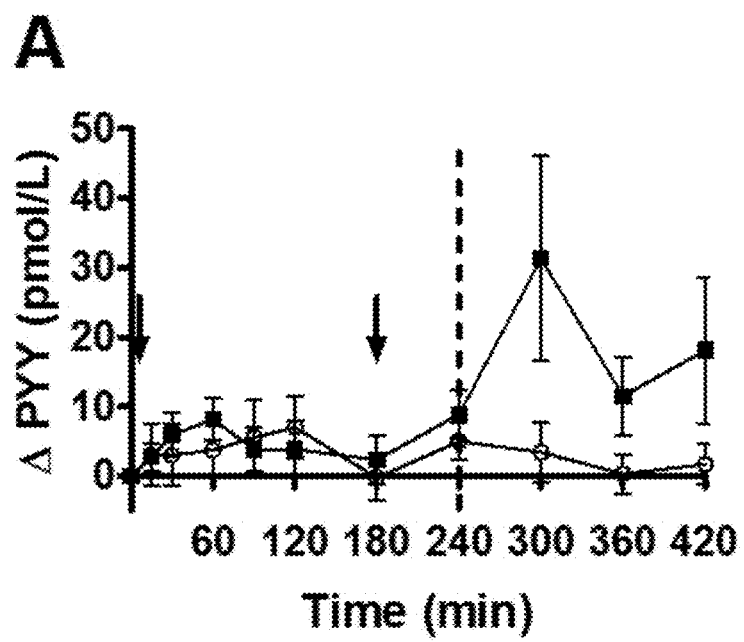
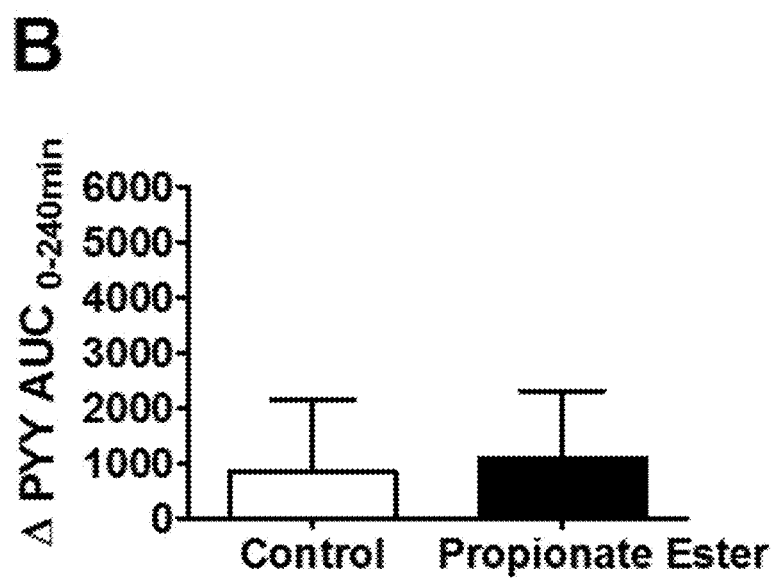

Figure 9 cont'd
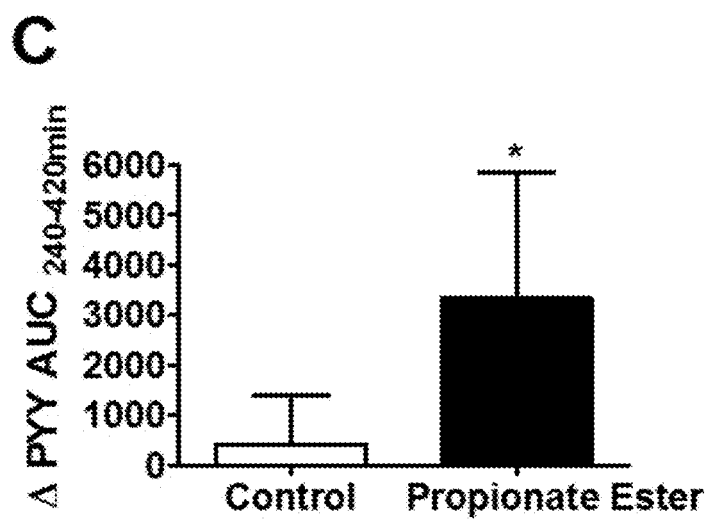
* = p > 0.05
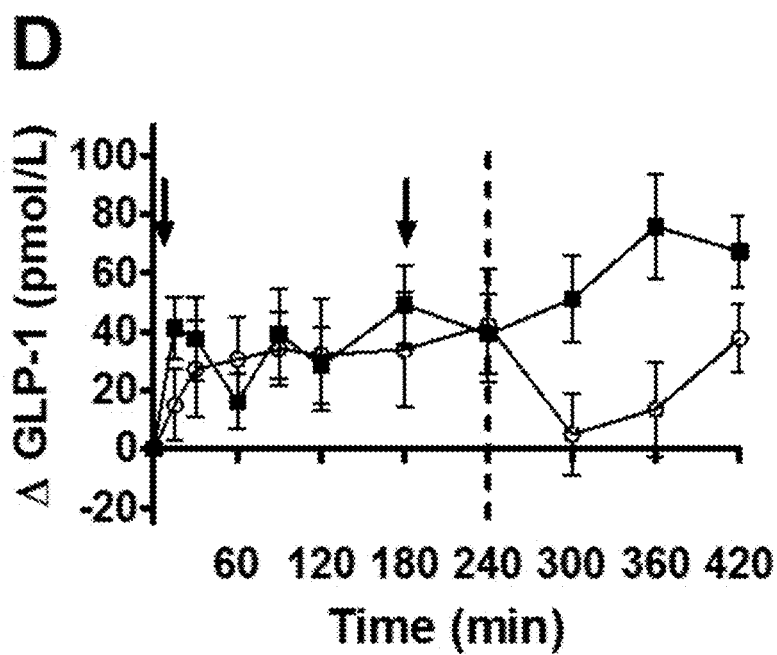

* = p > 0.05

Figure 11
A
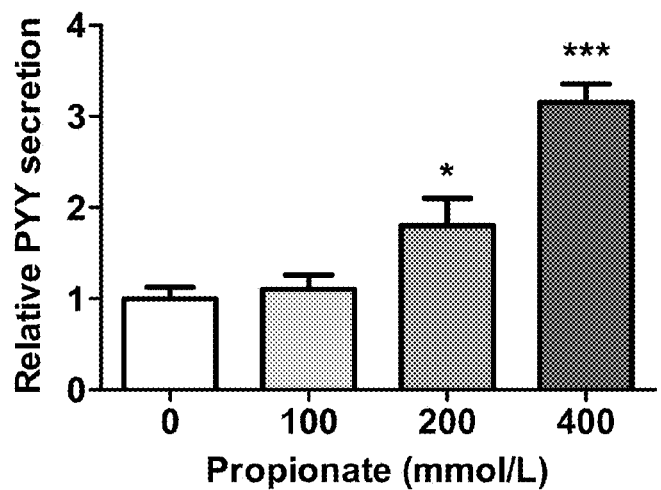
\* = p > 0.05
\*\*\* = p > 0.001
B
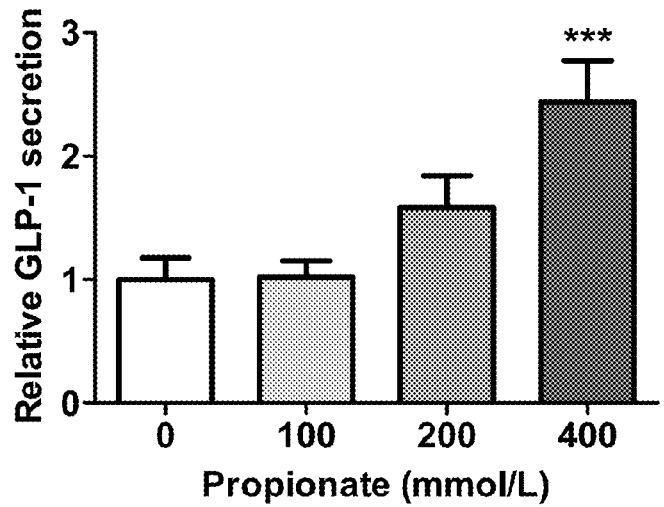
\*\*\* = p > 0.001

Figure 13

| | Propionate Ester (N = 25) | | | Control (N = 24) | | | P Value (Propionate Ester vs. Control) |
|---|---|---|---|---|---|---|---|
| | Week 0 | Week 24 | P Value | Week 0 | Week 24 | P Value | |
| Sex (no. of subjects) | | | | | | | |
| Male | 10 | | | 9 | | | |
| Female | 15 | | | 15 | | | |
| Race or ethnicity (no. of subjects) | | | | | | | |
| White | 16 | | | 18 | | | |
| Black | 4 | | | 2 | | | |
| Asian | 5 | | | 4 | | | |
| Age (yr) | 55.3 ± 7.0 | | | 53.4 ± 7.5 | | | |
| Weight (kg) | 88.5 ± 14.6 | 87.4 ± 14.8 | 0.062 | 91.0 ± 13.9 | 91.4 ± 14.7 | 0.558 | 0.097 |
| Body Mass Index (kg/m2) | 30.6 ± 3.5 | 30.2 ± 3.3 | 0.066 | 31.9 ± 3.7 | 31.8 ± 3.5 | 0.544 | 0.091 |
| Glucose (mmol/L) | 5.0 ± 0.5 | 5.0 ± 0.5 | 0.898 | 5.0 ± 0.5 | 5.0 ± 0.6 | 0.624 | 0.648 |
| Insulin (μU/mL) | 9.0 ± 4.6 | 8.8 ± 3.9 | 0.702 | 10.2 ± 3.9 | 10.0 ± 3.1 | 0.716 | 0.935 |
| HOMA-IR | 2.0 ± 1.1 | 2.0 ± 0.9 | 0.643 | 2.3 ± 1.0 | 2.2 ± 0.9 | 0.808 | 0.946 |
| HbA1c (mmol/mol) | 38.2 ± 3.3 | 37.8 ± 3.5 | 0.297 | 37.6 ± 2.6 | 37.1 ± 2.4 | 0.086 | 0.968 |
| Triglycerides (mmol/L) | 1.5 ± 0.8 | 1.4 ± 0.7 | 0.224 | 1.4 ± 0.8 | 1.6 ± 1.2 | 0.266 | 0.100 |
| Cholesterol (mmol/L) | | | | | | | |
| Total | 5.5 ± 1.0 | 5.1 ± 1.0 | <0.001 | 5.3 ± 0.9 | 5.0 ± 0.9 | 0.014 | 0.480 |
| Low-density lipoprotein | 3.5 ± 0.9 | 3.2 ± 0.8 | 0.001 | 3.3 ± 0.8 | 3.1 ± 0.9 | 0.126 | 0.622 |
| High-density lipoprotein | 1.4 ± 0.3 | 1.2 ± 0.2 | 0.004 | 1.4 ± 0.3 | 1.2 ± 0.3 | <0.001 | 0.677 |
| Liver function tests (IU/L) | | | | | | | |
| Alanine Transaminase | 28.3 ± 13.5 | 23.9 ± 11.7 | 0.015 | 34.5 ± 19.4 | 27.0 ± 14.9 | 0.001 | 0.202 |
| Alkaline Phosphatase | 75.8 ± 17.9 | 70.5 ± 16.3 | <0.001 | 78.1 ± 17.2 | 71.7 ± 16.5 | <0.001 | 0.565 |
| Aspartate Transaminase | 28.5 ± 5.2 | 25.6 ± 4.4 | 0.007 | 29.0 ± 6.9 | 30.6 ± 12.3 | 0.540 | 0.119 |

| AT Distribution (% Total AT) | Propionate Ester (N = 17) | | | Control (N = 15) | | | P Value (Propionate Ester vs. Control) |
|---|---|---|---|---|---|---|---|
| | Week 0 | Week 24 | P Value | Week 0 | Week 24 | P Value | |
| Subcutaneous AT | 76.3 ± 1.3 | 76.0 ± 1.6 | 0.633 | 81.3 ± 1.9 | 80.6 ± 1.8 | 0.002 | 0.385 |
| Internal AT | 23.7 ± 1.7 | 24.0 ± 1.6 | 0.518 | 18.7 ± 1.9 | 19.4 ± 1.8 | 0.001 | 0.277 |
| Abdominal Internal AT | 13.2 ± 1.2 | 13.1 ± 1.1 | 0.977 | 10.6 ± 1.3 | 11.1 ± 1.4 | <0.001 | 0.040 |
| Abdominal Subcutaneous AT | 21.9 ± 0.7 | 21.6 ± 0.7 | 0.170 | 23.1 ± 0.9 | 22.7 ± 0.8 | 0.314 | 0.936 |
| $^1$H-MRS (Geometric mean) | | | | | | | |
| IHCL | 15.75 ± 4.86 | 11.50 ± 3.55 | 0.038 | 7.83 ± 2.77 | 7.42 ± 2.43 | 0.515 | 0.139 |
| Soleus IMCL | 21.80 ± 2.96 | 23.95 ± 3.72 | 0.273 | 18.75 ± 1.91 | 18.78 ± 1.71 | 0.864 | 0.362 |
| Tibilalis IMCL | 9.07 ± 0.98 | 9.48 ± 0.88 | 0.657 | 10.03 ± 1.44 | 10.26 ± 1.06 | 0.732 | 0.963 |

AT, adipose tissue; MRS, magnetic resonance spectroscopy; IHCL, intrahepatocellular lipid; IMCL, intramyocellular lipid. Mean ± SEM.

Figure 16

| Treatment | Time (h) | Bacterial concentration (Log₁₀cells/ml culture fluid) | | | | | | | | | | | | |
|---|---|---|---|---|---|---|---|---|---|---|---|---|---|---|
| | | Probe | | | | | | | | | | | | |
| | | Bif164 | | Bac303 | | Ato201 | | Lab158 | | Chis150 | | Erec482 | | EUB338 I II III |
| A propionate ester (dₑ = 0.74) | 0 | 8.57 | (0.09) | 8.67 | (0.17) | 8.61 | (0.16) | 7.07 | (0.19) | 7.88 | (0.09) | 8.91 | (0.19) | 9.75 (0.07) |
| | 10 | 8.62 | (0.10) | 9.07‡ | (0.12) | 8.90 | (0.35) | 7.07 | (0.39) | 7.84 | (0.28) | 9.06 | (0.24) | 9.87 (0.08) |
| | 24 | 8.34 | (0.14) | 9.50‡ | (0.03) | 9.65† | (0.36) | 7.52 | (0.34) | 8.00 | (0.24) | 8.72 | (0.47) | 10.10 (0.08) |
| | 34 | 8.62 | (0.28) | 9.80‡ | (0.10) | 9.81* | (0.06) | 7.25 | (0.23) | 8.00 | (0.61) | 8.97 | (0.38) | 9.69 (0.01) |
| | 48 | 8.81 | (0.38) | 9.76‡ | (0.10) | 9.64† | (0.26) | 7.21 | (0.39) | 8.08 | (0.23) | 9.05 | (0.43) | 10.24 (0.09) |
| B inulin control | 0 | 8.57 | (0.09) | 8.67 | (0.17) | 8.61 | (0.16) | 7.07 | (0.19) | 7.88 | (0.09) | 8.91 | (0.19) | 9.75 (0.07) |
| | 10 | 9.36† | (0.14) | 9.37‡ | (0.16) | 9.11† | (0.06) | 7.36 | (0.23) | 7.76 | (0.31) | 8.46 | (0.21) | 10.43 (0.17) |
| | 24 | 9.37‡ | (0.27) | 9.42‡ | (0.15) | 9.60† | (0.25) | 7.62 | (0.34) | 7.76 | (0.30) | 8.75 | (0.17) | 9.96 (0.11) |
| | 34 | 9.43† | (0.12) | 9.49‡ | (0.08) | 9.52* | (0.19) | 7.49 | (0.27) | 7.69 | (0.54) | 9.01 | (0.21) | 10.57 (0.09) |
| | 48 | 9.59‡ | (0.22) | 9.21† | (0.10) | 9.33 | (0.50) | 7.06 | (0.55) | 7.42 | (0.13) | 9.09 | (0.17) | 10.46 (0.13) |
| C control-no substrate | 0 | 8.57 | (0.09) | 8.67 | (0.17) | 8.61 | (0.16) | 7.07 | (0.19) | 7.88 | (0.09) | 8.91 | (0.19) | 9.75 (0.07) |
| | 10 | 8.30 | (0.06) | 8.61 | (0.02) | 8.74 | (0.32) | 7.44 | (0.23) | 7.80 | (0.12) | 8.46 | (0.14) | 9.76 (0.04) |
| | 24 | 8.30 | (0.20) | 8.74 | (0.10) | 9.06 | (0.04) | 7.61 | (0.14) | 7.65 | (0.25) | 8.25 | (0.27) | 10.51 (0.14) |
| | 34 | 8.36 | (0.17) | 8.91 | (0.25) | 8.84 | (0.12) | 7.50 | (0.24) | 7.86 | (0.17) | 8.45 | (0.28) | 10.39 (0.02) |
| | 48 | 8.16 | (0.05) | 8.75 | (0.27) | 8.91 | (0.16) | 7.38 | (0.32) | 7.56 | (0.05) | 8.58 | (0.20) | 9.81 (0.14) |

*P = <0.05

COMPOUNDS AND THEIR EFFECTS ON APPETITE CONTROL AND INSULIN SENSITIVITY

This application is a National Stage Application of PCT/GB2013/052056, filed Jul. 31, 2013, which claims priority to United Kingdom Patent Application No. 1213629.7, filed Jul. 31, 2012, which is incorporated in its entirety by reference herein.

FIELD OF THE INVENTION

This application relates to the use of propionate inulin esters to control appetite, food intake and/or calorie intake and/or to improve insulin sensitivity, particularly in the field of obesity and diabetes.

BACKGROUND OF THE INVENTION

Obesity and its associated diseases, including type 2 diabetes, coronary heart disease and certain forms of cancers, are major public health challenges for the 21st century. The World Health Organisation (WHO) has declared that global childhood and adult obesity levels have reached epidemic proportions with the incidence in both developed and developing countries increasing at an alarming rate (WHO, Obesity: Preventing and managing the global epidemic, Report on a WHO Consultation, 2000). It is predicted that up to 58% of the world's adult population will be overweight or obese by 2030 (Kelly, T., et al., Int. J. Obes. 32:1431-7, 2008).

Diabetes is a chronic disease which occurs when the pancreas does not produce enough insulin (type 1 diabetes) or when the body cannot effectively use the insulin it produces (type 2 diabetes). Type 2 diabetes, which is related to being overweight, obesity and physical inactivity, accounts for around 90% of all cases of diabetes, and the number of cases is increasing globally. WHO predict that diabetes deaths will double between 2005 and 2030 (WHO Fact Sheet No. 312, 2011), so that by 2030 diabetes will become the seventh leading cause of death world-wide.

Disease risk related to obesity, such as type 2 diabetes disease risk or cardiovascular disease risk, increases independently with increased body mass index (BMI). This risk has been quantified as a five percent increase in the risk of cardiac disease for females, and a seven percent increase in the risk of cardiac disease for males, for each point of a BMI greater than 24.9 (see Kenchaiah, M. D., et al., *N. Engl. J Med.* 347:305, 2002; Massie, B. M., *N. Engl. J Med.* 347:358, 2002). In addition, there is substantial evidence that weight loss in obese persons reduces important disease risk factors. Even a small weight loss, such as 10% of the initial body weight, in both overweight and obese adults has been associated with a decrease in risk factors such as hypertension, hyperlipidemia, and hyperglycemia. Recently it has been shown that considerable weight loss can effectively cure type 2 diabetes (Lim, E. L., et al, Diabetologia 54:2506-14, 2011).

The cause of obesity is complex and multi-factorial. Increasing evidence suggests that obesity is not a simple problem of self-control but is a complex disorder involving appetite regulation and energy metabolism. Although the etiology of obesity is not definitively established, genetic, metabolic, biochemical, cultural and psychosocial factors are believed to contribute.

Diet and exercise provide a simple process to decrease weight gain, however overweight and obese individuals often cannot sufficiently control those factors to effectively lose weight. Pharmacotherapy is available; several weight loss drugs have been approved by the Food and Drug Administration that can be used as part of a comprehensive weight loss program. However, many of these drugs have proved to have serious adverse side effects and have had to be withdrawn. An acceptable pharmacotherapy must be acceptable for use over an extended period of time, and so risks of side-effects must be low. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients.

It is not only obese subjects who may wish to lose weight. People with weight in, for example, the upper part of the recommended range, may wish to reduce their weight to bring it closer to the ideal weight, or those with a healthy weight may wish to have assistance in maintaining that weight by preventing gaining weight. Thus, a need remains for agents that can be used to effect weight loss in overweight and obese subjects as well as subjects who are of normal weight.

The Foresight report highlighted appetite regulation as a major target in the dietary treatment of obesity (Butland, B. J., et al., Foresight Tackling Obesities: Future Choices—Project Report, Government Office for Science, 2007). Of particular interest is the concept of functional foods or novel products which increase satiety. The goal is to design foods or dietary regimens that increase the sense of fullness and encourage the individual to stop eating sooner, thus reducing total energy intake (Hill, J. O., Peters, J. C., Br. *J. Nutr.* 88(suppl. 2):S213-8, 2002).

One goal of a successful pharmacotherapy or dietary treatment of obesity would be that it could be applicable at a public health level. This means a cost-effective treatment that can be safely applied at the population level to improve appetite regulation and prevent weight gain throughout life. An attractive strategy is the enrichment of foods with components that reduce appetite, food intake and/or calorie intake. A composition which could be added to staple food stuffs, such as bread, with no noticeable effect on palatability, would be easily accessible to the wider population and so applicable at a public health level.

There currently remains a need for further pharmacotherapy and dietary treatments of obesity which successfully regulate appetite, food intake and/or calorie intake, as well as such treatments which do not have unpleasant side effects. There also remains a need for pharmacotherapy and dietary treatments that can prevent weight gain in healthy or overweight subjects. The aim of the current inventors is to identify a treatment that reduces appetite, food intake and/or calorie intake and/or that can improve insulin sensitivity in a subject, and which may be applicable at a public health level.

SUMMARY OF THE INVENTION

The invention provides a propionate inulin ester ("PE") for the reduction of appetite, food intake and/or calorie intake and/or to improve insulin sensitivity in a subject.

The invention also provides a propionate inulin ester for the treatment or prevention of obesity or diabetes.

The present invention is based on the finding by the present inventors that orally administered propionate inulin ester reduces appetite, food intake and calorie intake, increases satiety and improves inulin sensitivity in humans.

The invention further provides certain novel propionate inulin esters.

BRIEF DESCRIPTION OF THE DRAWINGS

FIG. 4(a) shows the effects of propionate inulin ester with varying $d_e$ on total food intake from meals taken over a 7 hour period; and 4(b) shows the effects of propionate inulin ester with varying $d_e$ on food intake from ad libitum meals taken 7 hours after ingestion of the propionate inulin ester.

FIG. 7(a) shows food intake 7 hours after intake of propionate inulin ester ($d_e$=0.74, 10 g) compared to inulin; and FIG. 7(b) shows an individual analysis of food intake in 20 subjects 7 hours after intake of propionate inulin ester supplement ($d_e$=0.74, 10 g).

FIGS. 11(a) and (b) show the levels of PYY and GLP-1 released from primary human colonic cells after incubation with propionate.

FIG. 13 show the baseline characteristics of subjects and changes in cardiovascular and diabetes risk factors following 24 weeks of propionate inulin ester ($d_e$=0.74) and inulin control supplementation.

FIG. 15 shows mean body fat depots at baseline (week 0) and following 24 weeks of propionate inulin ester ($d_e$=0.74) and inulin control supplementation (week 24).

FIG. 16 shows bacterial concentrations ($Log_{10}$ cells/ml) of *Bifidobacterium* spp (Bif164), *Bacteroides/Prevotella* (Bac303), *Lactobacillus/Enterococcus* (Erec482), *Clostridium histolyticum* (Chis150), *Atopobium* cluster (Ato291), *Eubacterium rectale/Clostridium coccoides* (Erec482) and total bacteria (EUB338 I II III) in culture fluid at 0, 10, 24, 34 and 48 h after anaerobic, pH controlled faecal batch culture fermentation with propionate inulin ester ($d_e$=0.74) (A), inulin control (B) and control-no substrate (C).

DEFINITIONS

Figure 1:
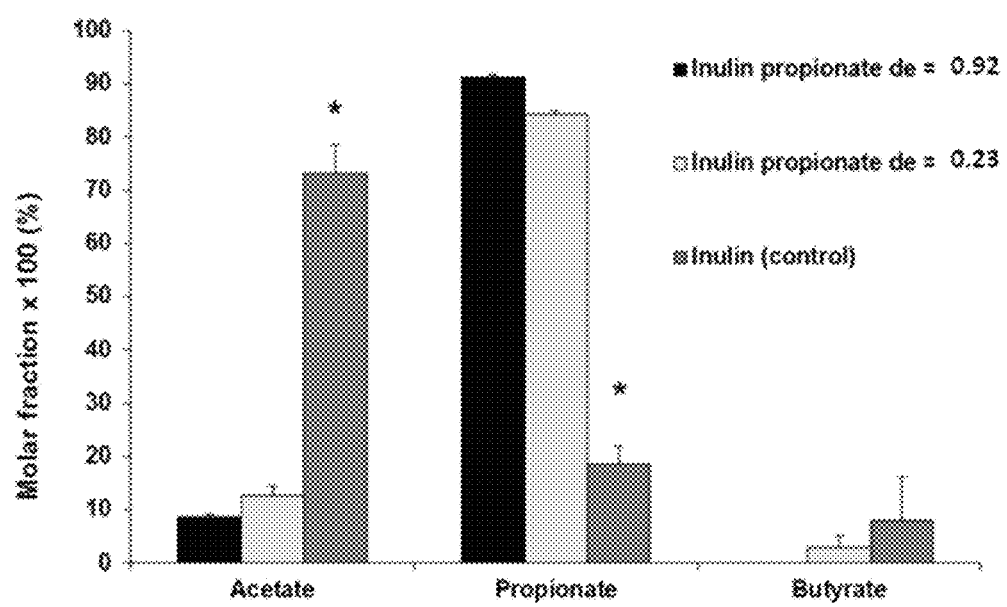
FIG. 1 shows the molar ratios of short chain fatty acids in batches of faecal cultures after ingestion of propionate inulin esters of varying degrees of esterification ($d_e$) compared to unsubstituted inulin.

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite can be measured by any means known to one of skill in the art. For example, decreased appetite can be assessed by a psychological assessment related to perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify subject as obese. Grade I obesity (which is sometimes referred to as being "overweight" rather than obesity) corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, E., Am. J. Clin. Nutr. 45:1035-47, 1987). Ideal body weight will vary among species and individuals based on height, body build, bone structure, and sex.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset and treatment.

The two major forms of diabetes are both characterized by an inability to deliver insulin in an amount and with the precise timing that is needed for control of glucose homeostasis. Type 1 diabetes or insulin dependent diabetes mellitus (IDDM) is caused by the destruction of β cells, which results in insufficient levels of endogenous insulin. Type 2 diabetes, or non-insulin dependent diabetes, results from a defect in both the body's sensitivity to insulin, and a relative deficiency in insulin production. Type 2 diabetes is related to being overweight, obesity and physical inactivity.

Degree of Substitution: The degree of substitution ($d_e$) of a carbohydrate, for example inulin, is the average number of substituent groups attached per sugar unit. The $d_e$ of inulin propionate ester is the average number of propionate groups attached per fructose or glucose unit of the inulin molecule. The maximum $d_e$ of inulin propionate ester is 3 due to each fructose unit only having 3 free OH groups.

Food intake: The amount of food consumed by an individual. Food intake can be measured by volume or by weight or by calories. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Glucagon-like peptide 1 (GLP1): GLP1 is derived from the transcription product of the proglucagon gene. The biologically active forms of GLP1 are truncated forms known as GLP1$_{(7-37)}$ and GLP1$_{(7-36)}$-NH$_2$. The sequence of human GLP1 is available, for example, from http://www.ncbi.nlm.nih.gov/protein/?term=GLP1.

GPR43: GPR43, also known as Free Fatty Acid Receptor 2 (FFAR2) is a member of a homologous family of orphan G protein-coupled receptors is and is expressed on enteroendocrine L cells that release the hormones GLP-1 and PYY. Short chain fatty acids are ligands of GPR43, with the propionate having the strongest affinity for the receptor, followed by acetate. (Le Poul, E., et al, J. Biol. Chem. (2003), Vol. 278, pages 25481-25489). The sequence of human GLP1 is available, for example, from http://www.ncbi.nlm.nih.gov/protein/?term=FFAR2

Inulin: Inulin is a generic term to cover all β(2→1) glycosidic bonded linear fructans, often with a terminal glucose unit. Inulins with a terminal glucose are known as alpha-D-glucopyranosyl-[beta-D-fructofuranosyl](n-1)-D-fructofuranosides, abbreviated as GpyFn. Inulins without glucose are beta-D-fructopyranosyl-[D-fructofuranosyl](n-1)-D-fructofuranosides, abbreviated as FpyFn. In general, inulins derived from plants contain between 20 and several thousand fructose units. Smaller compounds are called fructo-oligosaccharides, the simplest being 1-kestose, which has 2 fructose units and 1 glucose unit.

Non-Digestible Carbohydrates (NDCs): NDCs are carbohydrates which are indigestible in the stomach and small intestine, but are broken down in the colon by the fermentation process of bacteria to SCFAs, bacterial biomass and other by-products. NDCs include inulin, pectin, fructo-oligosaccharide, β-glucans, L-rhamnose, arabinogalactan and galacto-ologosaccharides and galacto-oligosaccharides.

Normal Daily Diet: The average food intake for an individual of a given species. A normal daily diet can be expressed in terms of caloric intake, protein intake, carbohydrate intake, and/or fat intake. A normal daily diet in humans generally comprises about 2,800 calories.

In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow, S. E., and Dietz, W. H., Pediatrics 102:E29, 1998; National Institutes of Health, National Heart, Lung, and Blood Institute (NHLBI), Obes. Res. 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 kg/m$^2$ is overweight, while a BMI of 30 kg/m$^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki, J. M., et al., Am. Fam. Phys. 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m² to 29.9 kg/m²

Peptide YY (PYY): The term PYY as used herein refers to a peptide YY polypeptide, a hormone secreted into the blood by cells lining the lower small intestine (the ileum) and the colon. The sequence of human GLP1 is available, for example, from http://www.ncbi.nlm.nih.gov/protein/?term=pyy Peripheral Administration: Administration outside of the central nervous system. Peripheral administration does not include direct administration to the brain. Peripheral administration includes, but is not limited to intravascular, intravenous, intramuscular, subcutaneous, inhalation, oral, intraperitoneal, rectal, transdermal, sublingual or intranasal administration.

Short Chain Fatty Acids (SCFAs): Short Chain Fatty Acids are fatty acids with aliphatic tails of 6 or fewer carbons. SCFAs include carboxylic acids of 6 carbons or less, these include acetate, propionate and butyrate, as well as branched acids such as isobutyrate (2-methylpropionate) and isovalerate (3-methylbutyrate. The SCFAs acetate, propionate and butyrate are key end-products of colonic fermentation of NDC.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount in the context of the current invention is an amount sufficient to inhibit or halt weight gain, or an amount sufficient to decrease appetite, or an amount sufficient to reduce caloric intake or food intake or increase energy expenditure.

DETAILED DESCRIPTION

As described above, the invention provides the use of a propionate inulin ester, for the reduction of one or more of the following in a subject:
  appetite,
  food intake,
  calorie intake
and/or to improve insulin sensitivity.

In particular, the subject is one in need of a reduction of one or more of appetite, food intake, or calorie intake and/or of improved insulin sensitivity. In particular, the subject is one in need of a reduction of one or more of appetite, food intake, or calorie intake.

Accordingly, the invention provides the use of a propionate inulin ester for the treatment or prevention of obesity or diabetes. The invention also provides the use of a propionate inulin ester for control and maintenance of body weight in subjects with a normal weight.

It has been found by the current inventors that oral administration of propionate inulin ester to humans reduced food intake. For example, when subjects were given 10 g of inulin propionate ester ($d_e$=0.74), in a subsequent meal, they ate on average 162 calories less than a control group that was given inulin. The propionate inulin ester did not suppress subjective appetite responses, yet significantly reduced meal size.

The inventors have found that supplementing the diet with inulin propionate ester leads to increased satiety. This makes propionate esters a viable dietary treatment (including prophylactic prevention) for obesity. In many cases the propionate inulin esters of the present invention exhibit improved potency and/or longer duration of action and/or fewer side effects and/or better compliance than alternative pharmacotherapy and dietary treatments for obesity.

The inventors have also found that supplementing the diet with inulin propionate ester leads to decreased fatty acid output from the adipose tissue, leading to improved insulin sensitivity. This makes propionate esters a viable dietary treatment for diabetes. In many cases the propionate inulin esters of the present invention exhibit improved potency and/or longer duration of action and/or fewer side effects and/or better compliance than alternative pharmacotherapy and dietary treatments for diabetes.

It has also been found that increasing the dose of propionate inulin ester with constant degree of substitution led to a decreased desire to eat and an increased level of fullness in subjective appetite responses. For example, when subjects were given 10 g of inulin propionate ester ($d_e$=0.74), in a subsequent meal, they ate 13% less energy than the control ($p<0.05$).

It has been found by the current inventors that oral administration of propionate inulin ester to humans reduced food intake in a dose dependent manner with respect to the dose of propionate (i.e. degree of substitution of the propionate inulin ester) compared to a control of unsubstituted inulin. For example, when subjects were given 10 g of inulin propionate ester with degree of esterification 0.23, in a subsequent meal, they ate 1100 Kcal, whereas as when they were given 10 g of inulin propionate ester with a degree of esterification 0.74, they ate 950 Kcal (see FIG. 4(b)).

It has been found by the current inventors that long-term delivery of propionate inulin ester to humans by daily oral administration reduced food intake, prevented weight gain and increased weight loss after 16 weeks. For example in a 24 week randomised controlled trial, weight gain in the propionate inulin ester group was lower than for the control group (propionate inulin ester group lost a mean body weight of 1.02±0.57 kg (p=0.062); the control group gained 0.38±0.69 kg (p=0.558)), with significantly fewer volunteers gaining >3 or >5% body weight. A significant increase in rate of weight loss occurred in the propionate inulin ester group between weeks 16-24 (0.81±0.26 kg; p=0.002). A decrease in energy intake was observed in the propionate inulin ester group of 4% across the 24 weeks of the study.

In the same 24 week study the inventors found long-term administration of propionate inulin ester lead to a decrease in abdominal adipose tissue and a within group reduction in intracellular hepatic lipid content and a significantly lower post-prandial insulin sensitivity. A significant deterioration in postprandial glucose response occurred in the control group, which was not observed in the propionate inulin ester group. Increases in plasma PYY and GLP-1 were not observed during the 24 week study. Therefore, propionate inulin ester may protect against declining glucose homeostasis linked to body weight gain.

The present inventors have also found that propionate inulin ester and inulin reduce several risk factors for cardiovascular disease and diabetes: for example in the 24 week randomised control trial mentioned above, significant improvements in total cholesterol, LDL, HDL, alanine transaminase, alkaline phosphatase and aspartate transaminase were observed in the propionate inulin ester group, and significant improvements in cholesterol, HDL, alanine transaminase and alkaline phosphatase were observed in the control group.

Some inulin esters are known. For example, the synthesis of certain inulin propionate esters is reported in U.S. Pat. No. 5,877,144. Preferred propionate inulin esters for use in the invention have a degree of substitution between 0.1 and 1.2, preferably between 0.2 and 1, preferably between 0.55 and 1, more preferably between 0.6 and 1, most preferably between 0.7 and 0.9.

The inventors have investigated possible physiological mechanisms behind the observed effects.

Using an isotopically-labeled inulin propionate ester, the current inventors have observed that inulin propionate facilitates delivery of propionate to the large intestine. Inulin is a non-digestible carbohydrate. The inulin is bonded to the propionate by an ester bond which is not cleaved in the stomach or upper GI tract. It is only cleavable by bacterial fermentation in the colon. In the colon, the propionate is released from the inulin. Results from stable isotope experiments showed that >80% of the propionate load from the propionate ester is released in the colon. It has previously been reported that some carbohydrates may be used as short-chain fatty acid carriers (see for example U.S. Pat. No. 5,840,860). The specific use of inulin to carry propionate has not previously been reported.

The inventors have also found that sodium propionate induced stimulation of PYY release in isolated colonic cells. In humans, levels of PYY in the plasma were shown to increase with increased degree of substitution of propionate of the propionate inulin ester. It is postulated that release of PYY after the delivery of propionate to the colon may be involved in the food-intake reduction observed.

It appears that released propionate may be involved in the food-intake reduction. Given the current knowledge concerning effects of propionate in humans that would be a surprising finding: for example, a review by Darzi et al [Darzi, J. et al, Proc. Nutr. Soc. (2011) Vol. 70, pages 119-128], which considered some reports that propionate might have an effect on food intake concluded that there may not be a role of propionate in appetite regulation. Instead they suggest that the results of some earlier studies in which food intake reduction was suggested were due to lack of palatability of propionate and food-stuffs doped with propionate. In their own studies, reported in the same review, Darzi et al removed palatability as a factor and showed orally administered propionate had no effect of appetite or food intake. Another review by Al-Lahham et al [Al-Lahham, S. H., et al, Biochem. Biophys. Acta. (2010), Vol. 1801, pages 1175-1183.], reviewed the biological effects of propionic acid in humans. The review suggests that propionic acid may be beneficial in reducing food intake and improving satiety, but that it is possible that this effect is due to food aversion or nausea and discomfort.

Thus, while orally administered free propionate has been seen in some studies to have caused some reduction in food intake or appetite, the effects have mostly been put down to the reduced palatability of food containing propionate (it is very acidic) in combination with the side effects of discomfort and nausea when taking the free propionate. Oral propionic acid is absorbed in the proximal small intestine.

It appears that the invention by the current inventors enables propionate to be delivered to the large intestine and that it exerts its appetite reducing effect there. Further studies will be required, in order to add certainty to this postulated mechanism.

Compounds

Inulins have the general formula:

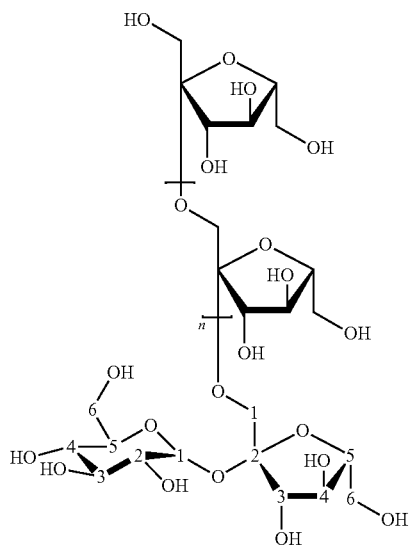

Inulins for use in the invention are preferably composed of fructose units connected by β (2→1) links, and generally are terminated by a glucose unit. Inulins may be extracted from chicory (*Cichorium intybus*), jerusalam artichoke (*Helianthus tuberosus*), or other sources of inulins, for example Elecampane (*Inula helenium*), Coneflower (*Echinacea* spp.), Dandelion (*Taraxacum officinale*), Wild yam (*Dioscorea* spp.), Jicama (*Pachyrhizus erosus*), Burdock (*Arctium lappa*), *Costus Saussurea lappa*, Mugwort (*Artemisia vulgaris*), Onion (*Allium cepa*), Garlic (*Allium sativum*), Agave (*Agave* spp.), Leopard's-bane (*Arnica montana*), Yacón (*Smallanthus sonchifolius* spp.), Camas (*Camassia* spp.) or Banana. Synthetic inulins may also be used.

Preferably, an inulin suitable for use in the invention is extracted from chicory or jerusalam artichoke, and most preferably chicory. An example of a commercially available source of inulin from chicory is Orafti® HP from Beneo-Orafti Food Ingredients, Tienen, Belgium.

The degree of polymerization (the number of monosaccharide units coupled together) of the inulin is between 2 and several thousand. Preferably the degree of polymerization is between 2 and 60, and more preferably between 3 and 60. The average degree of polymerization of the inulin of the invention is preferably between 20 and 30, more preferably between 23 and 27 and most preferably 25.

Inulin is a non-digestible carbohydrate. In humans it cannot be digested in the stomach or small intestine under the influence of enzymes, but requires the presence of bacteria in the large intestine/colon. The invention is applicable to any inulin or oligofructose which cannot be digested in the stomach or small intestine.

Propionate has the formula $CH_3CH_2CO_2-$. The corresponding carboxylic acid, propionic acid has the formula $CH_3CH_2CO_2H$.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The free acid or a salt of the active ingredient may be provided as a solvate.

Methods of Preparing Propionate Inulin Esters

Inulin propionate esters for use in the invention can be prepared in aqueous conditions, as follows: inulin is dissolved in water for example at 20 to 80° C. The concentration of the resulting solution is preferably between 0.2 and 4 moles of fructose equivalents per liter, more preferably between 1 and 2 moles of fructose equivalents per liter, and most preferably between 1.2 and 1.6 moles of fructose equivalents per liter. The temperature of the resulting solution is preferably lowered to between 10 and 20° C. Propionic anhydride and a metal base, preferably an aqueous alkali metal base, more preferably a metal hydroxide, for example sodium hydroxide or potassium hydroxide, are added to the inulin solution, preferably keeping the temperate between 10 and 20° C. and the pH of the solution between pH 8 and 8.5. The base is preferably in aqueous solution of between 10 and 100% w/v, preferably between 20 and 100% w/v, more preferably between 20 and 40% w/v and most preferably 25% w/v and is added dropwise to the inulin solution. Varying the ratio of propionic anhydride to inulin produces varying degree of substitution. The number of moles of propionic anhydride to be added to the inulin is calculated as: moles of fructose unit equivalents×target degree of substitution×1.25. Table 1 shows example ratios to be used.

| Target Degree of Esterification ($d_e$) | Ratio Propionic Anhydride: Inulin (mol/mol) |
|---|---|
| 0.2 | 0.25:1 |
| 0.5 | 0.625:1 |
| 0.8 | 1:1 |
| 1.0 | 1.25:1 |

This synthesis is suitable for synthesis of inulin propionate esters with degree of substitution between 0.05 and 3.0. Preferably, this synthesis is used for synthesis of inulin propionate esters with degree of substitution between 0.1 and 2.0, more preferably between 0.1 and 1.5, and most preferably for synthesis of inulin propionate esters with degree of substitution between 0.1 and 1.

The invention provides propionate inulin esters preparable by dissolving inulin in water at between 20 and 80° C. to give a concentration of between 1 and 2 moles of fructose equivalents per liter, lowering the temperature of the solution to between 10 and 20° C., adding propionic anhydride and an aqueous metal base with a concentration between 20 and 100% w/v to the solution while keeping the temperate of the solution between 10 and 20° C. and the pH of the solution between pH 8 and 8.5; to give the desired degree of substitution the number of moles of propionic anhydride added to the inulin is calculated as: number of moles of fructose unit equivalents in solution×target degree of substitution×1.25.

Inulin propionate esters for use in the invention may be synthesised in organic solvents, such as polar aprotic solvents, for example, but not limited to, N,N'-dimethylacetamide, dimethyl sulfoxide, dimethylformamide, using similar reaction methodology as for the aqueous reaction, but where water is substituted for solvent.

Preferably, inulin propionates of the invention are synthesised in aqueous conditions.

Inulin propionate esters synthesised according to the above aqueous method can by purified to remove free propionate, which thereby improves their palatability and reduces possible side effects from ingesting free propionate. Preferably purification is carried out using activated charcoal columns under acidic conditions followed by spray drying. For example, after completion of the synthesis as described above, or to propionate inulin ester dissolved in water to give a solution with a concentration of between 0.2 and 4 moles of fructose equivalents per liter, more preferably between 1 and 2 moles of fructose equivalents per liter, and most preferably between 1.2 and 1.6 moles of fructose equivalents per liter, the reaction mixture or solution is adjusted to between pH 1.5 and pH 3.5, more preferably to between pH 2 and pH 3 and most preferably to pH 2, with concentrated strong acid, for example a strong inorganic acid, for example HCl. Immediately after addition of acid the reaction mixture is allowed to flow through an activated charcoal column which has been thoroughly washed and conditioned with between 0.05 and 0.5 M strong acid, preferably between 0.1 and 0.3 M strong acid, most preferably 0.2 M strong acid, for example a strong inorganic acid, for example HCl. The propionate inulin ester is allowed to flow through the column at approximately 1 L/hr. The size of charcoal column is selected depending on number of moles of fructose equivalents in the solution, for example for a 2 L solution containing approximately 2.8 moles of fructose units, a column containing ~1 kg activated charcoal is suitable. Activated carbon has a higher affinity and sequestration capacity for propionic acid compared with the anionic form—propionate. The reaction mixture recovered from the column is adjusted to pH 2 with concentrated strong acid, for example a strong inorganic acid, for example HCl, and passed through a second activated charcoal column prepared in an identical or similar fashion to the first column. The reaction mixture is collected and adjusted to pH 2 before spray drying (Buchi, Oldham UK) in an inert $N_2$ gas flow. The flow of liquid, gas and nebulizer temperature are controlled such that an outlet temperature of around 100° C. is maintained.

Preferably, propionate inulin esters for use in the invention are purified to a level of free propionate in the propionate inulin ester of less than 1% but preferably completely free of unbound propionate.

The invention provides a method of purifying a propionate inulin ester, comprising dissolution of propionate inulin ester in water, adjusting the pH of the solution to around pH 2 with concentrated strong acid, passing the solution though an activated charcoal column washed and conditioned with 0.2 M strong acid, recovering the solution from the column, adjusting to around pH 2 with concentrated strong acid, passing the solution through a second activated charcoal column washed and conditioned with 0.2 M strong acid, recovering the solution from the column, adjusting to around pH 2 with concentrated strong acid and spray drying.

Purification of propionate inulin ester can also be achieved using dialysis. Purification by dialysis in dialysis tubing is particularly effective; preferably dialysis is for a period of between 1 and 5 days, most preferably 3 days. Dialysis can be used for removal of any salt impurities, and removal of free propionate to a level of <1% of the total propionate available after full de-esterification. An example of suitable dialysis tubing is Spectra/Por 6, 1000 MWCO from Spectrum Europe B.V., Breda, Netherlands. For example, after 3-day dialysis in dialysis tubing, this results in propionate inulin ester that is almost tasteless when dissolved in water and undetectable when dissolved in fruit juice.

The taste of propionate leads to reduced palatability. After purification by dialysis the taste of free propionate is very low and can be easily masked with other flavours. This leads to increased palatability, which can lead to a higher level of patient compliance. It also reduces the possibility of side effects resulting from ingestion of residual free propionate, particularly when a large dose of propionate inulin ester is ingested.

The invention further provides a novel inulin propionate ester with degree of substitution of 0.55 to 1. U.S. Pat. No. 5,877,144 describes the synthesis of propionate inulin esters of degree of substitution=0.5.

The invention provides propionate inulin esters with $d_e$ between 0.55 and 1.0. Such propionate inulin esters are preparable by dissolving inulin in water, for example at between 70 and 80° C. to give a concentration of between 1 and 2 moles of fructose equivalents per liter, lowering the temperature of the solution to between 10 and 20° C., adding propionic anhydride and an aqueous alkali metal base with a concentration between 20 and 100% w/v to the solution whist keeping the temperate of the solution between 10 and 20° C. and the pH of the solution between pH 8 and 8.5; to give the desired degree of substitution the number of moles of propionic anhydride added to the inulin is calculated as: number of moles of fructose unit equivalents in solution×target degree of substitution×1.25, with the minimum target degree of substitution=0.55 and maximum target degree of substitution=1. It is important for temperature and pH to be controlled within the limits mentioned above, as they influence the mixing of reactants, and are necessary to control the degree of esterification.

Compositions

While it is possible for the active ingredient to be administered alone, it is preferable for it to be present in a pharmaceutical formulation or composition, or administered orally as a direct additive to food.

The invention provides a pharmaceutical composition comprising a propionate inulin ester, and one or more pharmaceutically acceptable excipients. The invention also provides a pharmaceutical composition comprising a propionate inulin ester, and one or more pharmaceutically acceptable excipients for use in the reduction of appetite, food intake and/or calorie intake and/or for improving insulin sensitivity, or for use in the treatment or prevention of obesity or diabetes. The invention further provides a pharmaceutical composition comprising a propionate inulin ester, and one or more pharmaceutically acceptable excipients for use in the reduction of appetite, food intake and/or calorie intake, and/or for use in the treatment or prevention of obesity.

The pharmaceutical formulations suitable for use in the invention include those suitable for oral administration. The most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10 (Supp. 42):25, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. An example of one suitable excipient is inulin. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compound can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavours, coloring agents and stabilizers may also be added for ease of fabrication and use.

The propionate inulin may be provided as a dry composition, for example a powder or granule form. It may be used for the preparation of a solution or a suspension for administration. A composition in the form of a concentrate or slurry may also be used for the preparation of a solution for administration. A composition suitable for preparing a solution, for example a powder or granule form or concentrate or slurry, may include a flavouring agent. A composition can be provided in a quantity for the preparation of a unit dose of a therapeutically effective amount, for example a dose between 50 ml and 1 L, for example a 500 ml dose. The invention provides a composition for a mixture with water.

The invention further provides a dry composition, for example a powder or granule form, for mixture with a foodstuff.

A solution or a suspension may be in an aqueous liquid or a non-aqueous liquid. The solution may include a flavouring agent and/or preservative agent.

A flavouring for use in compositions of the invention should, if applicable, mask any saltiness and/or acidic taste, and be stable in the composition. A flavouring makes the solutions more palatable and thus aids patient compliance. Preferred flavourings include orange, lemon, strawberry, grapefruit, blackcurrant, vanilla and lemon and lime.

If more than one unit is taken per dose, each unit may be in the same or different physical forms. If more than one dose is taken per day, each dose may be in the same or different physical forms. Components within each of the two or more compositions may be in the same or different physical forms. Preferred unit dosage formulations are those containing an effective dose, as recited below, or an appropriate fraction thereof, of the active ingredient.

The active ingredient may suitably be administered in a sustained-release system. Suitable examples of sustained-release systems include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound, for example, a sparingly soluble salt. Sustained-release systems may be administered orally or as an oral spray.

Although not usually necessary for use with the invention, preparations for administration can be suitably formulated to give controlled release of a compound. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the propionate inulin ester. These compositions exhibit certain biocompatibility features which allow a controlled release of the active substance. See U.S. Pat. No. 5,700,486.

An alternative approach for the delivery of propionate inulin ester orally is to incorporate it in a food that is otherwise normal. For example, it might be incorporated in a food that a subject might eat during a main meal, for example a breakfast cereal or bread, or that a subject might eat as a snack during the day, for example a biscuit or chocolate. By delivering propionate inulin ester as part of a meal, it is possible to induce the desired reduced appetite at the next meal, or another meal later in the day, or a meal taken the following day. For example, the food with propionate inulin ester incorporated in it would beneficially be eaten about 3 to 10 hours before the later meal, preferably between 4 an 8 hours before the later meal. This will make the subject content with a smaller portion of the later meal, or cause the subject to eat a smaller amount of a normal portion.

The propionate inulin ester is incorporated at a level that provides the subject with an appetite-reducing dose when he/she consumes the whole of (or a usual portion of) the food in question. A food stuff incorporating an appetite-reducing dose of propionate inulin ester can be termed a functional food. Examples of foods to which propionate inulin ester can be added include, but are not limited to, baked goods (for example bread), confectionery, milk, yogurt and fresh cheese, chocolate, ice cream, sauces, fruit preparations or for the preparation of fructose syrups. Propionate inulin ester can be used as a substitute for inulin in foodstuffs which could incorporate or would normally incorporate inulin. Propionate inulin ester can also be added to inulin, and an inulin and propionate inulin ester mixture can be used as substitute to using inulin alone in foodstuffs which could incorporate or would normally incorporate inulin.

Combinations

In one embodiment, the active ingredient is administered with a therapeutically effective amount of another agent, for example an additional appetite suppressant, an additional food-intake-reducing agent, a plasma glucose-lowering agent or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. The active ingredient in the use of the invention can be administered simultaneously with the additional appetite suppressant, or it may be administered sequentially.

Thus, the invention provides, in an embodiment, a composition comprising a propionate inulin ester, and an additional appetite suppressant.

Such a composition is provided for use as a medicament, for example for use as a medicament for the treatment or prevention of obesity or diabetes, for example obesity.

The invention also provides a kit comprising:

a propionate inulin ester, and an additional appetite suppressant, the two (or more) components being for co-administration simultaneously, separately or sequentially.

Dosages

The therapeutically effective amount of a compound that should be administered depends on the propionate inulin ester utilized (including the specific inulin, the degree of substitution of propionate), the subject being treated, the severity and type of the affliction, and the manner and route of administration.

Considering the amount of propionate inulin ester that is delivered, a therapeutically effective amount of may be from about 0.1 mg per kilogram (kg) body weight to about 500 mg per kg body weight, for example about 1 mg to about 250 mg per kg body weight, for example about 10 mg to about 180 mg per kg body weight, for example about 20 mg to about 150 mg per kg body weight, for example about 60 mg to about 125 mg per kg body weight. For example, a therapeutically effective amount may be from about 10 mg to about 40 g, for example from about 80 mg to about 20 g, for example from about 100 mg to about 15 g, for example from about 1 g to about 12 g, for example from about 5 g to about 10 g.

For oral administration, a therapeutically effective amount may be from about 10 mg to about 20 g, for example from about 50 mg to about 20 g, for example from about 100 mg to about 20 g, for example from about 100 mg to about 10 g, for example from about 500 mg to about 10 g, for example from 500 mg to 5 g, for example from 500 mg to 2 g, for example from 1 g to 15 g, for example from 1 g to 10 g, for example from 1 g to 8 g, for example from 1 g to 2 g, for example from 1 g to 4 g, for example from 2 g to 4 g, for example from 2 g to 6 g, for example from 4 g to 8 g, for example from 4 g to 6 g, for example from 5 g to 10 g, for example from 6 g to 10 g, for example from 6 g to 8 g, for example from 8 g to 12 g, for example from 8 g to 10 g, for example from 10 g to 14 g, for example from 10 g to 12 g, for example from 10 g to 20 g. In a preferred embodiment, a therapeutically effective amount may be from about 10 mg to about 50 g, for example 10 mg to about 30 g, for example from about 50 mg to about 30 g, for example from about 100 mg to about 30 g, for example from about 100 mg to about 15 g or for example from about 500 mg to about 15 g. In another preferred embodiment, a therapeutically effective amount may be from about from 1 g to 50 g, for example from 5 g to 50 g, for example from 10 g to 40 g, for example 1 g to 30 g for example from 5 g to 30 g, for example from 3 g to 25 g, for example from 1 g to 20 g, for example from 5 g to 20 g, for example from 1 g to 10 g, for example from 20 g to 30 g, for example from 30 g to 40 g, or for example from 5 g to 15 g. Specific dosages that may be mentioned are 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5 and 15.0, especially 5.0, 5.5, 6.0, 6.5, 7.0, 7.5, 8.0, 8.5, 9.0, 9.5, 10.0, 10.5, 11.0, 11.5 and 12.0 g.

Each dose of a therapeutically effective amount may be several unit doses. A single solid unit dose may contain, for example, from about 50 mg to about 3 g, for example from about 100 mg to about 2 g, for example from about 250 mg to about 2 g, for example from about 500 mg to about 2 g, for example from about 250 mg to about 1 g, for example for example from about 500 mg to about 1 g, for example 100 mg to 500 mg, for example 100 mg to 1 g, for example 100 mg to 2 g, for example 250 mg to 2 g, for example 250 mg to 1 g, for example 500 mg to 2 g, for example 500 mg to 1 g, for example 1 g to 3 g, for example 1 g to 2 g. Specific unit doses that may be mentioned are 0.1, 0.25, 0.5, 0.6, 0.75, 0.8, 1.0, 1.25, 1.5, 1.75, 2.0, 2.25, 2.5, 2.75 and 3.0 g.

A single dry unit dose suitable for dissolution or addition to a liquid, or for dissolution or addition to a foodstuff, or a dose in solution or concentrate dose or slurry dose, may contain, for example, from about 100 mg to about 15 g, for example from about 250 mg to about 15 g, for example from about 500 mg to about 15 g, for example from about 500 mg to about 10 g, for example from about 500 mg to about 5 g, for example for example from about 500 mg to about 3 g, for example 100 mg to 1 g, for example 100 mg to 3 g, for example 1 g to 15 g, for example 1 g to 10 g, for example 1 g to 5 g, for example 1 g to 3 g, for example 1 g to 2 g, for example 2 g to 10 g, for example 2 g to 5 g, for example 5 g to 15 g, for example 5 g to 10 g, for example 250 mg to 1.5 g, for example 2 g to 4 g, for example 2 g to 6 g, for example 4 g to 6 g, for example 4 g to 8 g, for example 6 g to 8 g, for example 6 g to 10 g, for example 8 g to 10 g, for example 8 g to 12 g, for example 10 g to 12 g, for example 10 g to 14 g, for example 15 g to 20 g. Specific unit doses that may be mentioned are 0.25, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5 and 17.0.

The dose amounts discussed above may be given, for example, once, twice, three-times or four-times a day or once or twice a week. For example, for oral administration, a total daily dose of from 30 mg to about 120 g may be given, for example from about 240 mg to about 60 g, for example from about 300 mg to about 45 g, for example from about 3 g to about 36 g or for example from about 15 g to about 30 g. In one preferred embodiment, the total daily dose for oral administration is, for example from about 1 g to about 50 g, for example from about 1 g to about 30 g, for example from about 5 g to about 30 g, for example from about 5 g to about 25 g, for example from about 5 g to about 15 g or for example about 10 g. In another preferred embodiment, the total daily dose for oral administration is, for example from about 3 g to about 50 g, for example about 5 g to about 40 g, for example about 8 g to about 30 g, for example about 10 g to about 25 g, for example about 10 g to about 20 g, for example about 12 g to about 18 g or for example about 15 g.

According to a certain embodiment, a dose may be administered once between 4 and 10 hours before each meal to be taken. A dose may be administered between 4 and 10 before the effect (e.g., appetite suppression, decreased food intake and/or decreased caloric intake and/or improved insulin sensitivity) is desired, such as, but not limited to between 4 and 10 hours, between 5 and 9 hours, between 6 and 8 hours, about 4 hours, about 5 hours, about 6 hours, about 7 hours, about 8 hours, about 9 hours or about 10 hours before the time the effect is desired, for example at those times before a meal. Where the propionate inulin ester is administered as "functional food" the dose may be administered as part of the meal, or as a snack taken about 3 to 10 hours, preferably about 4 to 10 hours, and more preferably about 4 to 8 hours, before the later meal to be taken when the effect is desired.

In an embodiment, a dose is administered three times per day, for example three times at from about 4 hours to 10 hours before a meal, or during each meal as part of the meal to have an effect at another meal taken later that day or the following day. In that embodiment, the total daily dose may be from about 0.3 mg per kilogram (kg) body weight to about 1.5 per kg body weight, for example about 3 mg to about 750 mg per kg body weight, for example about 30 mg to about 540 mg per kg body weight, for example about 60 mg to about 450 mg per kg body weight, for example about 180 mg to about 375 mg per kg body weight. For example, a therapeutically effective amount may be from about 30 mg to about 120 g, for example from about 240 mg to about 60 g, for example from about 300 mg to about 45 g, for example from about 3 g to about 36 g, for example from about 15 g to about 30 g.

In an embodiment, a dose is administered as part of a meal or snack. An example of a part of a meal or a snack may be two slices of bread. In that embodiment two slices of bread may contain from about 100 mg to about 15 g, for example from about 1 g to about 12 g, for example from about 5 g to about 10 g of propionate inulin ester. An example of a snack may be a biscuit. In that embodiment a biscuit may contain from about 100 mg to about 15 g, for example from about 1 g to about 12 g, for example from about 5 g to about 10 g of propionate inulin ester. In another example, in a meal or snack which comprises flour as an ingredient, in that meal or snack from about 100 mg to about 15 g, for example from about 1 g to about 12 g, for example from about 5 g to about 10 g of the flour is replaced with the same weight of propionate inulin ester. In another example, in a meal or snack that contains a sauce or that comprises of a liquid or gel part, for example pasta sauce or yogurt, from about 100 mg to about 15 g, for example from about 1 g to about 15 g, for example from about 1 g to about 12 g, for example from about 5 g to about 10 g, of propionate inulin ester is mixed into the sauce or liquid or gel part.

In an embodiment, a dose is administered as part of a meal or snack or liquid, wherein the subject is provided with a dry dose for mixing with or combining with the meal, snack or liquid (for example water or fruit juice).

The propionate inulin ester of the invention finds particular use in conjunction with a hypocalorific diet. Many subjects find it difficult to adhere to a hypocalorific diet. The current invention promotes adherence to a hypocalorific diet.

Conditions:

The invention provides a propionate inulin ester for use in the reduction of one or more of the following in a subject:
appetite,
food intake,
calorie intake,
and/or to improve insulin sensitivity.

Accordingly, the invention provides a propionate inulin ester for use in the treatment or prevention of obesity or diabetes. For example, the invention provides a propionate inulin ester for use in the treatment or prevention of obesity.

Typically, the subject is overweight, or at risk of becoming overweight. The invention provides a propionate inulin ester, for the reduction of appetite in a subject, for use in the reduction of food intake in a subject, or for the reduction of calorie intake in a subject. The invention further provides a propionate inulin ester for use in improving insulin sensitivity.

The subject may be overweight, for example, obese. In certain embodiments, the propionate inulin ester is for use in the reduction of appetite, food intake and/or calorie intake and/or to improve insulin sensitivity in a subject who is overweight, for example obese.

Alternatively, or in addition, the subject may be diabetic, for example having insulin resistance or glucose intolerance, or both. The subject may have diabetes mellitus, for example, the subject may have type 2 diabetes. The subject may be overweight, for example, obese and have diabetes mellitus, for example, type 2 diabetes. In certain embodiments, the propionate inulin ester is for use in the reduction of appetite, food intake and/or calorie intake and/or to improve insulin sensitivity in a subject who is diabetic, who has insulin resistance and/or glucose intolerance.

The invention may be used for weight control and treatment, for example preventing and reducing weight gain; inducing and promoting weight loss; and reducing obesity as measured by the Body Mass Index. The invention may be used in the control of any one or more of appetite, food intake and/or calorie intake, in particular any one or more of the following: reducing, suppressing and inhibiting appetite; reducing, suppressing and inhibiting food intake; reducing, suppressing and inhibiting calorie intake. A compound of the invention may be used in maintaining any one or more of a desired body weight, a desired Body Mass Index, a desired appearance and good health.

A subject may be a subject who desires weight loss, for example a female or a male subject who desires a change in her or his appearance. A subject may desire decreased feelings of hunger, for example the subject may be a person involved in a lengthy task that requires a high level of concentration, for example a soldier on active duty, an air traffic controller, or a truck driver on a long distance route.

In certain embodiments, the invention provides use of a propionate inulin ester for the reduction of appetite, food intake and/or calorie intake in a healthy subject (for example having a normal BMI).

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, P. G., *Nature* 404:635-43, 2000; Rissanen, A., et al., *British Med. J.* 301:835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e. g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

According to certain embodiments, the subject may have a non-desired weight despite not being obese or overweight. Such use may relate to subjects who were previously overweight or obese and who wish to prevent a return to an unhealthy weight. It may also relate to subjects with a pre-diabetic state such as insulin insensitivity or pre-diabetes. In some cases where the subject is of a normal weight, aspects of the invention may relate to cosmetic treatment rather than to therapeutic treatment.

The invention may also be used in treating, preventing, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

The subject is preferably a human. However, the subject may also be another vertebrate, for example other primates; farm animals for example swine, cattle and poultry; sport animals for example horses; or companion animals for example dogs and cats.

EXAMPLES

The invention is illustrated by the following non-limiting Examples.

Example 1a

Synthesis and Characterisation of Propionate Inulin Esters

Materials and Methods
Synthetic Method 450 g inulin (110.5 mmoles or 2.8 moles fructose equivalents, Orafti® HP from Beneo-Orafti Food Ingredients, Tienen, Belgium: average degree of polymerization=25; average MW=4071 Da; minimum level of polymerization=3) was dissolved in 2 L deionised water and transferred to a 3 L water-cooled jacketed reactor with overhead stirring and continuous pH monitoring and allowed to cool to ~25° C. 360 g propionic anhydride (2.8 moles) and 550 ml 25% w/v NaOH were set up in dropper funnels above the reactor. The pH was adjusted to 8.25 by dropwise addition of NaOH and the addition of propionic anhydride commenced when the temperature in the reaction mixture was <20° C. The rate of addition of reagents was such that the pH remained between 8-8.5 and the temperature remained <20° C. Varying the ratio of propionic anhydride to inulin, as follows, produced products of varying $d_e$:

| Target Degree of Esterification ($d_e$) | Ratio Propionic Anhydride:Inulin (mol/mol fructose equivalents) | Observed Product Degree of Esterification ($d_e$) |
|---|---|---|
| 0.2 | 0.25:1 | 0.18 |
| 0.25 | 0.31:1 | 0.23 |
| 0.5 | 0.625:1 | 0.46 |
| 0.8 | 1:1 | 0.74 |
| 1.0 | 1.25:1 | 0.92 |

Once addition was complete the reaction mixture was allowed to pH stabilize and thereafter adjusted to pH 2 with concentrated HCl. Immediately, the reaction mixture was allowed to flow through a charcoal column which had been thoroughly washed and conditioned with 0.2 M HCl. The column contained ~1 kg activated charcoal and was allowed to flow through at approximately 1 L/hr. Activated carbon has a higher affinity and sequestration capacity for propionic acid compared with the anionic form—propionate. The reaction mixture recovered from the column was adjusted to pH 2 with concentrated HCl and passed through a second column prepared in an identical fashion to the first column. The final collected mixture was collected and again adjusted to pH 2 before spray drying (Buchi, Oldham UK) in an inert $N_2$ gas flow. The flow of liquid, gas and nebulizer temperature were such that an outlet temperature of 100° C. was maintained.

Propionate Inulin Ester Characterisation
Chemical Characterisation
Infrared Spectroscopy Infrared (FT-IR, Perkin Elmer, Cambridgeshire UK) spectra were recorded using KBr discs.

Analysis of Propionate Content by GC-FID 100 mg of propionate inulin ester product was dissolved in 2 ml water containing 1 mM butyric acid as internal standard (IS). To quantify free propionate, 200 μl of the solution was treated with 100 μl of concentrated orthophosphoric acid followed immediately by ether extraction (1 ml). To quantify total propionate (free+bound), another 200 μl of the solution was treated with 100 μl of concentrated orthophosphoric acid and heated at 80° C. for 1 hour before being extracted with 1 ml ether. The ether extracts were decanted to clean vials ready for gas chromatography (GC) analysis. Propionate and butyrate were quantified by GC analysis (HP5790, Palo Alto, USA) using a ZB-WAX column (30 m×0.32 mm×0.25 um; Phenomenex, Cheshire UK) and He as carrier gas (1.8 ml/min) in split injection (~50:1 split ratio). The temperature program started at 40° C. and was held for 1 minute before ramping at 10° C./min to 200° C. Detection was carried out by flame ionization detection (FID). External standards were run daily to calculate the FID response factor and peak area ratios extracted to an Excel spreadsheet for data processing. Propionate concentration was calculated relative to the IS and the yield of free and total propionate calculated per g ester from the different treatments.

Propionate yield was calculated relative to the IS and the amount of free propionate calculated by the ratio (free/total)×100(%). The degree of esterification ($d_e$) was also calculated using this analysis by using the yield of bound propionate (total−free) per gram of ester to compute moles of propionate yielded per mole of propionate ester.

Purity Characterisation
Salt Content

The salt content of 12 random batches of the propionate inulin ester produced over the period of ~1 year was tested externally by an accredited food laboratory (Alcontrol Laboratories, Rotherham, UK). The results were expressed as g/g×100(%) content.

Heavy Metals Screening

Toxic heavy metals (As, Cr, Cd & Pb) content was measured against an external calibrating standard by inductively coupled plasma-optical emission spectroscopy (ICP-OES; Optima 7300 DV, Perkin Elmer Cambridgeshire UK). Inulin and propionate inulin ester samples were dissolved in Analar concentrated nitric acid and diluted 1:100 before analysis with reference to the external calibrant. Results (μg/g) were expressed as determined by the instrument.

Microbiological Screening

Microbiological quality of 12 random propionate inulin ester batches produced over the period of ~1 year was tested externally by an accredited food testing laboratory (Alcontrol Laboratories, Bellshill, UK). The samples were tested for aerobic colony counts (cfu/g), enterobacteriaceae (cfu/g), *E. Coli* (cfu/g) and *Listeria* (in 25 g).

Results
Synthesis

The yield of propionate inulin ester from inulin was ~70%.

Chemical Characterization
Infrared Spectroscopy

The characteristic vibration of an ester group was observed at 1736.8 cm$^{-1}$ which was not present in the starting inulin product.

GC-FID

GC analysis (n=12) yielded 2.57±0.26% free propionate of the total propionate yielded from the molecule on complete de-esterification. Analysis of the total yield of propionate (and accounting for free propionate) from the molecule showed that the actual degree of esterification ($d_e$) achieved was 0.74±0.02.

Purity

Analysis of the salt content showed that 25.9±0.5% (n=12) of the final weight could be attributed to NaCl.

Heavy metal screening showed that all IPE samples had heavy metal contents below that of the commercially sourced parent compound and were <1 µg/g for all species.

The results of the microbiological testing indicated <20 cfu/g aerobic colony, <10 cfu/g enterobacteriaceae, <10 cfu/g E. Coli and "not detected" for Listeria (in 25 g) in all samples tested, well below the accepted thresholds for ready-to-eat foodstuffs (22).

Example 1b

Synthesis and Characterisation of $^{13}C$ Labeled Propionate Inulin Esters

Materials and Methods

A $^{13}C$ stable isotope labeled variant of the propionate inulin ester was synthesised in an identical fashion as described above for propionate inulin ester, using $^{13}C$-propionic anhydride as a starting material, to produce $^{13}C$-propionate ester with $(1-^{13}C_1)$-propionate bound to inulin.

Results

Labeled propionate inulin ester was synthesized with a predicted $d_e$ of 0.74. This prediction is based on the assumption that the $d_e$ of the labeled propionate inulin ester will be the same as the unlabeled propionate inulin ester, as the same synthetic methodology and same ratios of propionate to ester were used (1:1).

Example 2

In Vitro Testing of Propionate Inulin Ester Digestibility and Fermentability

Materials and Methods

The fermentation profiles of inulin propionate ester with $d_e=0.23$ and inulin propionate ester with $d_e=0.92$ were tested using batch faecal cultures. The faecal sample was collected from one healthy female and prepared in triplicate incubations for each treatment. Batch faecal cultures were prepared at a concentration of 1% (wet wt/vol) in PBS (pH 7, 100 mM) using a standard kitchen blender to homogenize the sample. 50 ml of this slurry were transferred to gas tight, crimp top 100 ml serum vials and ~100 mg of the NDC ester to be tested was added. Vials were flushed with oxygen free nitrogen immediately and placed into a shaking water bath held at 37° C. 800 µl of the aqueous volume was removed from each vial every at 0, 2, 4 and 6 hour intervals. 100 µl of IS (2-ethylbutyrate, 73.8 mM) and 100 µl concentrated orthophosphoric acid were added and the sample thoroughly mixed and immediately extracted with 3×3 ml ether. The ether aliquots were pooled and a sub-sample transferred to a clean vial for analysis. Samples were analyzed by GC-FID as previously described and the concentration of acetate, propionate and butyrate reported at each time-point using the area ratio to the IS and the calibrated response factor of each SCFA to the IS determined by a gravimetrically prepared external standard.

Results

FIG. 1 shows that the proportion of propionate produced from propionate inulin ester in faecal fermentations is significantly higher compared with inulin and accounts for ~90% of the total SCFA produced.

Example 3

The Effects of Propionate Inulin Ester with Varying $d_e$ on Subjective Measures of Appetite and Hunger Rating, Food Intake and Metabolic Response in Human Subjects Material and Methods
Study Protocols Nine healthy subjects (8 males and 1 female) were recruited to investigate the effect of increasing $d_e$ in propionate inulin ester. The mean (±SEM) age body mass index (BMI) was 26±2 years and 23.9±2.1 kg/m$^2$, respectively.

The criteria for exclusion were smoking, substance abuse, pregnancy, use of medications (except for oral contraceptives), a change in body weight >5 kg in the previous 3 months, medical or psychiatric illness, and any abnormalities detected on physical examination, electrocardiography, or screening blood tests (measurement of complete blood count, electrolytes, fasting glucose, thyroid function and liver function). All subjects provided informed, written consent prior to the clinical trial (Registration No: NCT00750438), which was approved by the Hammersmith and Queen Charlotte's Research Ethics Committee (08/H0707/99). The study was carried out in accordance with the Declaration of Helsinki.

The study was performed over a 4 week period starting with control (10 g inulin) and thereafter increasing dose of propionate per week (IPE $d_e=0.23$, $d_e=0.46$, $d_e=0.74$ in subsequent weeks, approximating to 10, 20 and 30 wt % propionate intake respectively). The protocol consisted in any given week of 2 days dose acclimatization, study day on day 3 followed by 4 days of washout. Subjects refrained from alcohol and strenuous exercise for the 24 hours prior to each study day and consumed an identical meal between 19:00 and 20:00 the evening before. Subjects then fasted overnight and arrived at Hammersmith Hospital at 08:30 on each study day. A cannula was inserted into a forearm vein and baseline blood samples were collected at −10 and 0 min. Following the 0 min sample, subjects were served a standardized breakfast (398 kcal; 71.2 g CHO, 7.9 g fat, 10.3 g protein) containing either the test vector. At 180 min a standardized lunch (356 kcal; 34.2 g CHO, 11.9 g fat, 28.1 g protein) was provided and at 420 min subjects were offered a buffet dinner with food served in excess to satisfy all appetites. Food intake was calculated by weighing the food served preprandially and the food not eaten postprandially. Postprandial blood samples were taken at 15, 30, 60, 90, 120, 180, 240, 300, 360 and 420 min and collected into heparin-coated tubes containing 0.2 ml of aprotonin (Bayer). Plasma was separated immediately by centrifugation (3000 rpm for 10 minutes) at 4° C. and then stored at −70° C. until it was analyzed. Subjective hunger, satiety, and nausea were monitored with the use of 100 mm VAS. Subjects were asked to complete the VAS before each blood sample. Breath $H_2$ was measured at 0, 60, 120, 180, 240, 300, 360 and 420 min (Bedfont Scientific, Kent UK). Insulin-like immunoreactivity was measured using an ultra-sensitive human insulin radioimmunoassay (Millipore, USA). Plasma glucose was measured using an Abbott Architect ci8200 analyzer (Abbott Diagnostics, USA).

Data Analysis

Results are expressed as mean±SEM. Results were compared by AVOVA with post-hoc analysis. Statistical analysis was conducted on SPSS 18 (Chicago, USA).

Figure 2:
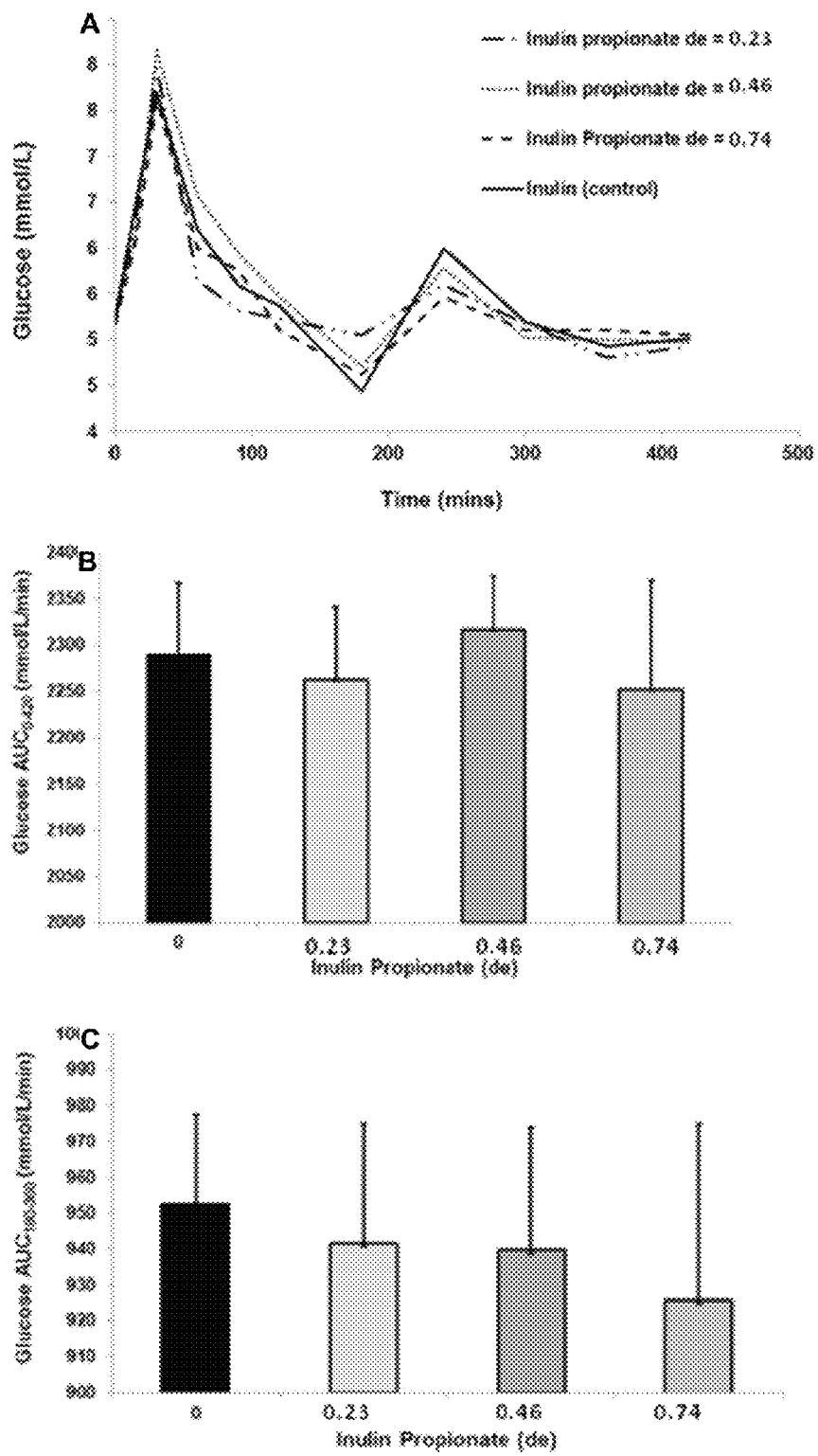
FIGS. 2(a) to (c) show the effects of propionate inulin ester with varying $d_e$ on blood glucose levels.
Figure 3:
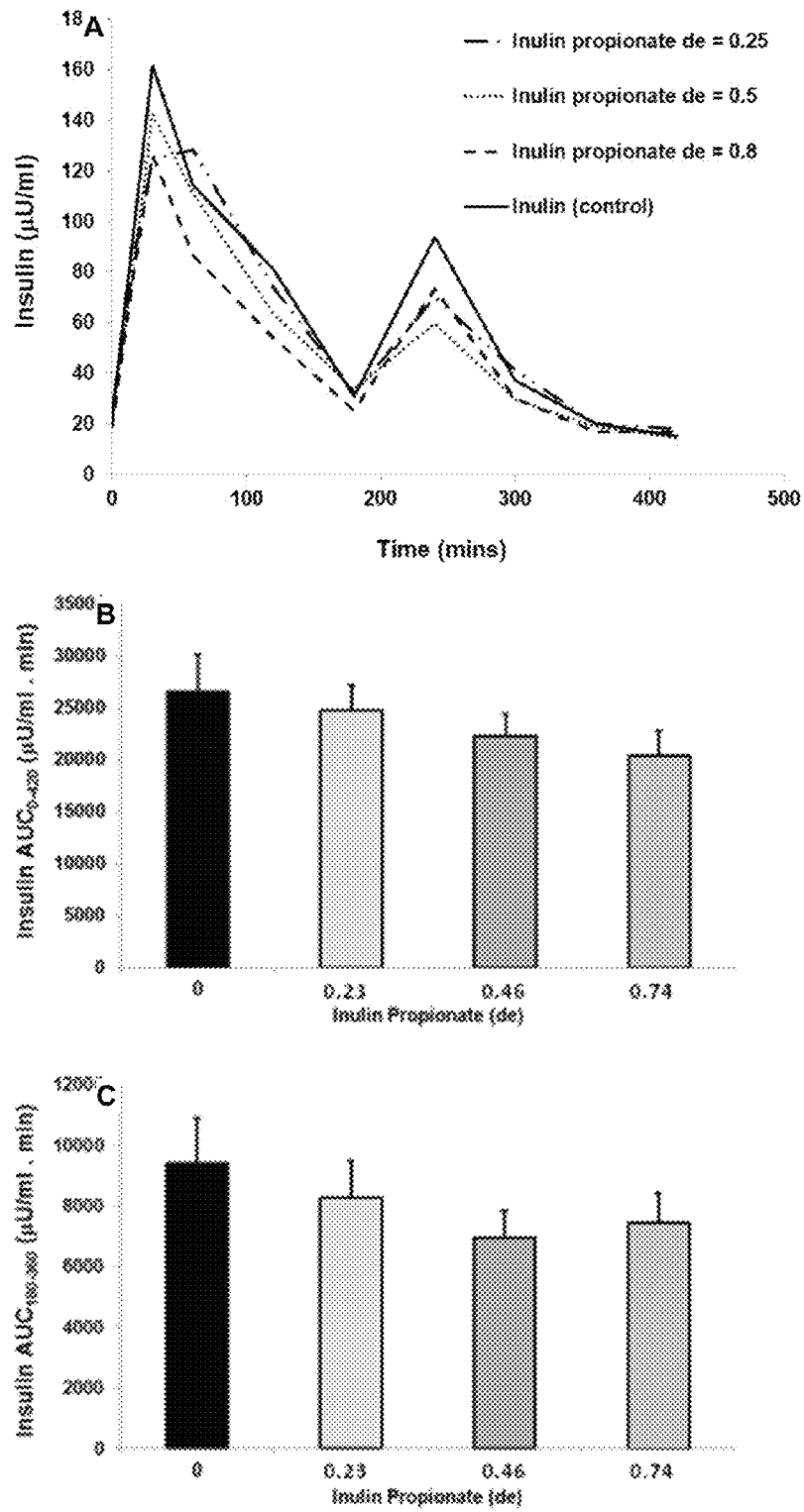
FIGS. 3(a) to (c) show the effects of propionate inulin ester with varying $d_e$ on blood insulin levels.

Results:

In vivo there was a significant linear trend (p<0.02) for reduced glucose concentrations in the period when maximal propionate flux would occur (FIG. 2(c), $AUC_{180-360}$) although overall glucose $AUC_{0-420}$ showed no significant attenuation (FIG. 2(b). A significant linear trend (p<0.01) was also observed for insulin response over the study protocol (FIG. 3(b), $AUC_{0-420}$) but not during maximal propionate flux (FIG. 3(c) $AUC_{180-360}$, p=0.167). A significant linear trend (p=0.03) was observed from baseline to propionate inulin ester with $d_e$=0.46 which at higher $d_e$ appeared to plateau. No significant effect was observed when the treatments were analyzed per group for glucose or for insulin.

Food intake in the ad libitum meal taken 7 hours after ingestion of the propionate inulin ester (FIG. 4(b)) and food intake over the whole experiment (FIG. 4(a)) across the treatments exhibited a significant linear trend in reduced food intake with increasing propionate inulin ester $d_e$ (p=0.02 for food intake over whole experiment) but group comparisons showed no significant effect.

Example 4

The Effect of Different Propionate Inulin Ester ($d_e$=0.74) Doses (0, 5, 10 and 15 g) on Subjective Measures Appetite and Hunger Rating and Food Intake Study Protocols Nine healthy subjects (8 males and 1 female) were recruited to investigate the effect of increasing dose at fixed $d_e$ of propionate inulin ester. The mean (±SEM) age and body mass index (BMI) was 27±2 years and 25.0±1.3 kg/m², respectively.

The criteria for exclusion were smoking, substance abuse, pregnancy, use of medications (except for oral contraceptives), a change in body weight >5 kg in the previous 3 months, medical or psychiatric illness, and any abnormalities detected on physical examination, electrocardiography, or screening blood tests (measurement of complete blood count, electrolytes, fasting glucose, thyroid function and liver function). All subjects provided informed, written consent prior to the clinical trial (Registration No: NCT00750438), which was approved by the Hammersmith and Queen Charlotte's Research Ethics Committee (08/H0707/99). The study was carried out in accordance with the Declaration of Helsinki.

Subjects were studied on four occasions one week apart. Each week subjects arrived at Hammersmith Hospital at 08:30 and were served a standardized breakfast (533 kcal; 78.1 g CHO, 16.9 g fat, 17.5 g protein) containing an escalating dose of 0, 5, 10, 15 g IPE ($d_e$=0.74). This involved a 6-day run-in period on the given dose followed by the study day before moving to the next dose level. On each occasion they were given an identical dose of 100 mg $^{13}$C labeled propionate inulin ester ($d_e$=~0.74, containing ~30 mg of bound (1-$^{13}C_1$)-propionic acid). Breath $H_2$ was collected and measured in real-time using a handheld $H_2$ monitor (Bedfont Scientific Ltd, Kent UK). Breath $CO_2$ was collected serially over 24 hrs (excluding the sleep period) by exhaling alveolar breath through a straw into Exetainers. $^{13}CO_2$ enrichment was determined by isotope ratio mass spectrometry. Breath $H_2$ was expressed as ppm and $^{13}CO_2$ as ppm xs, defined as ppm $^{13}$C enrichment above baseline samples collected before isotope ingestion. Cumulative $^{13}CO_2$ excretion was also calculated.

At the beginning of the study subjects were served a standardized breakfast (398 kcal; 71.2 g CHO, 7.9 g fat, 10.3 g protein) containing the test dose+100 mg $^{13}$C-IPE. At 180 min a standardized lunch (356 kcal; 34.2 g CHO, 11.9 g fat, 28.1 g protein) was provided and at 420 min subjects were offered a buffet dinner with food served in excess to satisfy all appetites. Food intake was quantified by weighing the food preprandially and the uneaten food weighted postprandially. Subjective hunger, satiety, and nausea were monitored with the use of 100 mm VAS. Subjects were asked to complete the VAS at 15, 30, 60, 90, 120, 180, 240, 300, 360 and 420 min.

Data Analysis

Results are expressed as mean±SEM. Results were compared by AVOVA with post-hoc analysis. Statistical analysis was conducted on SPSS 18 (Chicago, USA).

Figure 5:
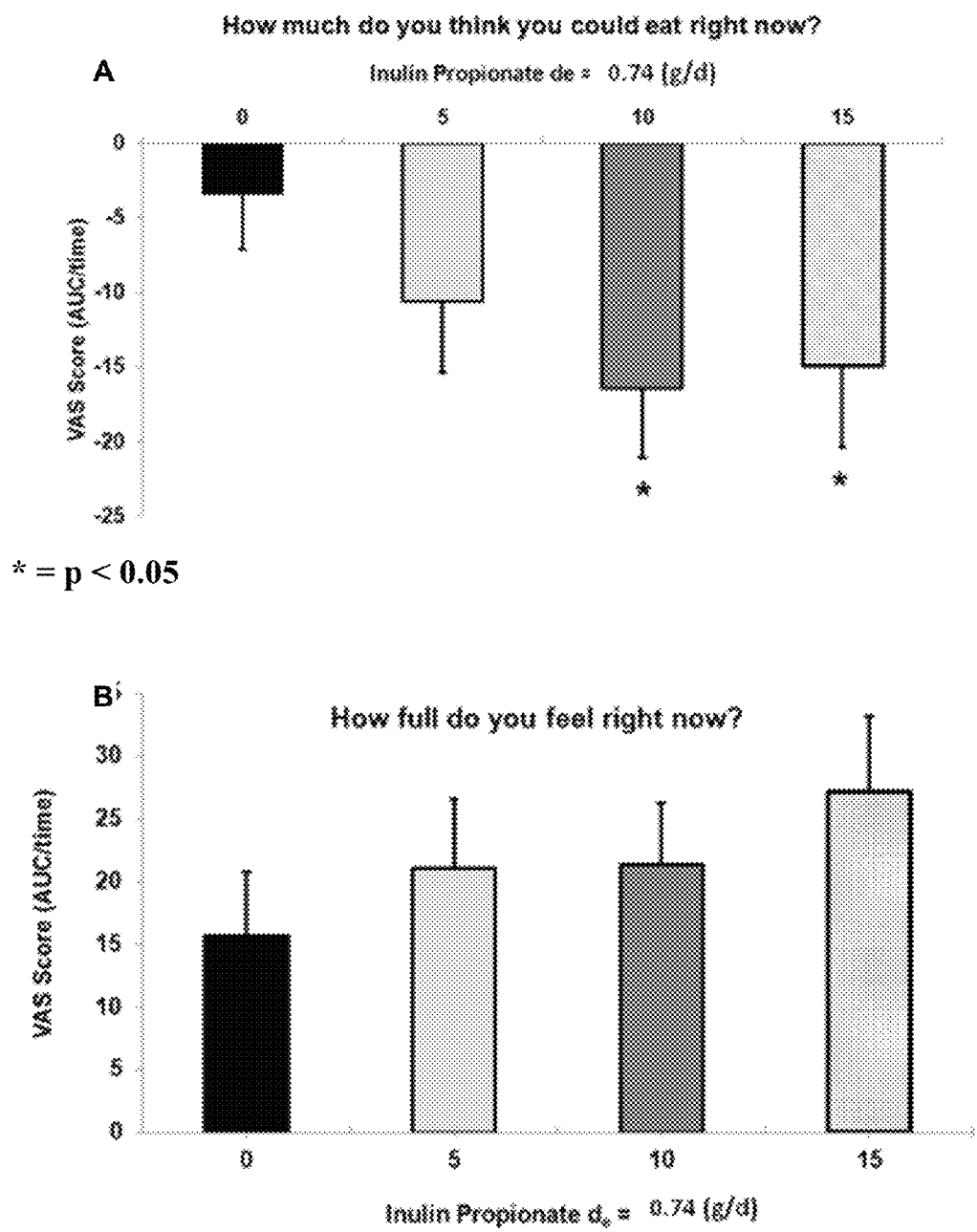
FIG. 5 shows subjective appetite ratings of desire to eat and fullness with increasing dose of inulin propionate ester ($d_e$=0.74) over a 7 hour period.

Results:

Food intake in relation to increased intake of propionate inulin ester ($d_e$=0.74) showed no significant decrease either in linear trend (p=0.12) or group analysis (p=0.9). FIG. 5(a) shows that feelings of wanting to eat assessed by VAS showed significant decreased desire to eat at 10 and 15 g doses of IPE (p<0.05). A significant linear trends towards decreased wanting to eat was only observed from baseline to 10 g (p=0.04) but not from baseline to 15 g (p=0.11) of propionate inulin ester intake. A significant linear trend (p=0.046) towards increased feelings of fullness with increasing dose of IPE was observed (FIG. 5(b)) although no significant effects was seen in the group comparisons.

Example 5

Stable Isotope Investigation

Study Subjects

Nine healthy subjects (8 males and 1 female) were recruited for the stable isotope investigation. The mean (±SEM) age, weight and body mass index (BMI) was 32±4 years, 75.0±4.0 kg and 25.0±1.3 kg/m², respectively.

The inclusion criteria for the investigation were a BMI of 20 to 35 kg/m² and 21 to 65 years of age. The exclusion criteria were smoking, substance abuse, pregnancy, use of medications (except for oral contraceptives), a change in body weight >5 kg in the previous 3 months, medical or psychiatric illness, restrained eating (Dutch eating behavior questionnaire: male score >2.25; female score >2.80), and any abnormalities detected on physical examination, electrocardiography, or screening blood tests (measurement of complete blood count, electrolytes, fasting glucose, thyroid function and liver function).

Subjects were studied on four occasions one week apart. Each week subjects arrived at Hammersmith Hospital at 08:30 and were served a standardized breakfast (533 kcal; 78.1 g CHO, 16.9 g fat, 17.5 g protein) containing an escalating dose of inulin propionate (0, 5, 10, 15 g). On each occasion they were given an identical dose of $^{13}C$ labeled inulin propionate containing ~30 mg of $(1-^{13}C_1)$-propionic acid ($d_e$=~0.74 containing ~30 mg of bound $(1-^{13}C_1)$-propionic acid). Breath $H_2$ was collected and measured in real-time using a handheld $H_2$ monitor (Bedfont Scientific Ltd, Kent UK). Breath $CO_2$ was collected by blowing into Exetainers. $^{13}CO_2$ enrichment was determined by isotope ratio mass spectrometry (IRMS). Breath $H_2$ was expressed as ppm and $^{13}CO_2$ as ppm xs, defined as ppm $^{13}C$ above baseline samples collected before isotope ingestion. Cumulative $^{13}CO_2$ excretion was also calculated. Blood was collected serially throughout the study.

Plasma was collected at −15, 0, 15, 30, 60, 90, 120, 180, 240, 300, 360 min for analysis of $^{13}C$ propionate enrichment by GC-combustion-IRMS (GC-C-IRMS). Acetate $^{13}C$ enrichment was also measured in the same analysis as a control for dietary influence on SCFA $^{13}C$ enrichment and for evidence of inter-conversion between propionate and acetate. Data were expressed as $\delta^{13}C$ (per mil or ‰) which represents the change in the measured ratio in parts per thousand from the internationally accepted standard carbon Vienna Pee Dee Belemnite (VPDB). Urine was analyzed for $^{13}C$ propionate by GC-C-IRMS. Urine was collected and pooled from just before consumption of the propionate ester for a period of 24 hours. Two 25 ml aliquots were collected and stored at −20° C. until analysis. Isotopic enrichment was expressed as $\delta^{13}C$ (‰). SCFA concentrations (mmol/L) were measured relative to an internal standard (3-methyl valerate).

Results:

$^{13}C$ propionate inulin ester, 82.9±2.3% of the propionate recovered in breath over 24 hours appeared co-incident with and after breath $H_2$ onset, defined as the first sustained rise in breath $H_2$, suggesting delivery of the majority of the tracer to the colon.

Data from sudden death victims shows the average propionate pool size in the proximal large intestine to be 4.5 mmol. We calculated that intake of 10 g propionate inulin ester, releasing 36.2 mmol propionate, would increase colonic propionate levels on average by ~800% should all propionate be released in the colon.

Figure 6:
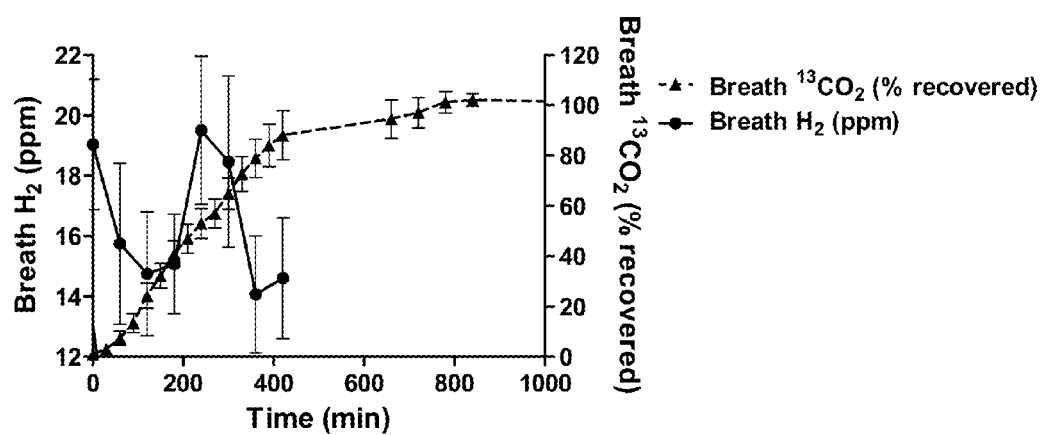
FIG. 6 shows the enrichment of $^{13}C$ in expired air (% recovered) and level of breath hydrogen (ppm) following consumption of $^{13}C$ labeled propionate inulin ester.

Propionate and breath hydrogen started to increase at 180 min, suggesting that the propionate inulin ester is being fermented (FIG. 6). Recovery of the labeled propionate continued to increase until 420 min when it reached a plateau. Where circulating plasma propionate was detectable, significant increases in propionate $^{13}C$ enrichment ($\delta^{13}C$=−18.4±1.6 vs. −2.5±3.3‰, p≤0.03, n=4) and concentration (13.4±1.4 vs. 23.7±2.2 µmol/L, p≤0.05, n=4) were measured in peripheral blood at 360 min compared with baseline. No significant differences were observed in plasma acetate enrichment or concentration. In urine, $^{13}C$ propionate enrichment was significantly higher with 10 g propionate inulin ester compared with control inulin ($\delta^{13}C$=−23.3±1.8 vs. −13.6±3.4‰; p=0.02; n=5), although no significant differences were seen in urinary propionate concentrations. The isotopic data demonstrate that propionate enters the blood stream and becomes available systemically.

Example 6

Food Intake Investigation in Human Subjects

Materials and Methods:
Propionate Inulin Ester

Propionate inulin ester was produced with a degree of esterification, $d_e$=0.74±0.02 (n=12) and a level of free propionate of 2.57±0.26% (n=12) of the total propionate available from the molecule. 97% of recovered propionate was chemically bound to the inulin polymer.

Study Subjects

Twenty healthy subjects (15 males and 5 females) were recruited for the food intake investigation. The mean (±SEM) age, weight and body mass index (BMI) was 31±2 years, 75.0±3.0 kg and 25.4±0.8 kg/m², respectively.

The inclusion criteria for the investigation were a BMI of 20 to 35 kg/m² and 21 to 65 years of age. The exclusion criteria were smoking, substance abuse, pregnancy, use of medications (except for oral contraceptives), a change in body weight >5 kg in the previous 3 months, medical or psychiatric illness, restrained eating (Dutch eating behavior questionnaire: male score >2.25; female score >2.80), and any abnormalities detected on physical examination, electrocardiography, or screening blood tests (measurement of complete blood count, electrolytes, fasting glucose, thyroid function and liver function).

Food Intake Investigation

The study was performed in a randomized, double-blind, crossover manner, with each subject studied on two occasions >4 days apart. Subjects refrained from alcohol and strenuous exercise for the 24 hours prior to each study day and consumed an identical meal between 19:00 and 20:00 the evening before. Subjects then fasted overnight and arrived at Hammersmith Hospital at 08:30 on each study day. A cannula was inserted into a forearm vein and baseline blood samples were collected at −10 and 0 min. Following the 0 min sample, subjects were served a standardized breakfast (398 kcal; 71.2 g CHO, 7.9 g fat, 10.3 g protein) containing either 10 g of inulin propionate ester ($d_e$=0.74) or 10 g inulin. At 180 min a standardized lunch (356 kcal; 34.2 g CHO, 11.9 g fat, 28.1 g protein) was provided and at 420 min subjects were offered a buffet dinner with food served in excess to satisfy all appetites. The amount of food was quantified preprandially and postprandially, and energy intake was calculated. Postprandial blood samples were taken at 15, 30, 60, 90, 120, 180, 240, 300, 360 and 420 min and collected into heparin-coated tubes containing 0.2 ml of aprotonin (Bayer). Plasma was separated immediately by centrifugation at 4° C. and then stored at −70° C. until it was analyzed. Subjective hunger, satiety, and nausea were monitored with the use of 100 mm visual analog scales (VAS). Subjects were asked to complete the VAS before each blood sample. In addition, VAS were also completed to assess the palatability of the standardized breakfast. Breath $H_2$ was measured at 0, 60, 120, 180, 240, 300, 360 and 420 min (Bedfont Scientific, Kent UK).

Gut Hormone Analysis

GLP-1- and PYY-like immunoreactivity was measured using specific and sensitive in-house radioimmunoassays. Insulin-like immunoreactivity was measured using an ultra-sensitive human insulin radioimmunoassay (Millipore) and plasma glucose was measured using an Abbott Architect ci8200 analyser (Abbott Diagnostics, USA).

Statistical Analyses

Differences in energy intake and incremental area under the curve (iAUC) for plasma hormone levels and VAS between trials were assessed using Paired Student's t tests. Two-way (trial×time) repeated measures ANOVA was performed to determine differences in plasma hormone levels, VAS and breath hydrogen. Significant effects were followed up by post hoc comparisons (Dunnett). P values<0.05 were considered statistically significant. Data are presented as means±SEM.

Results

The Effect of Propionate Inulin Ester on Food Intake in Human Volunteers 7 Hours after Intake of Oral Propionate Inulin Ester.

Changes in appetite were assessed by measuring food intake during a standardised ad libitum buffet meal 7 hours after intake of either the propionate-ester or inulin supplement. Food intake was significantly reduced form 1175±104 kcal to 1013±94 kcal (p=0.009) which corresponds to an average reduction of 13.8% (See FIG. 7(a)). Individual analysis of the data revealed that 16 out of 20 subjects experienced a reduction in food intake under the propionate inulin ester supplement (See FIG. 7(b)).

Figure 8:
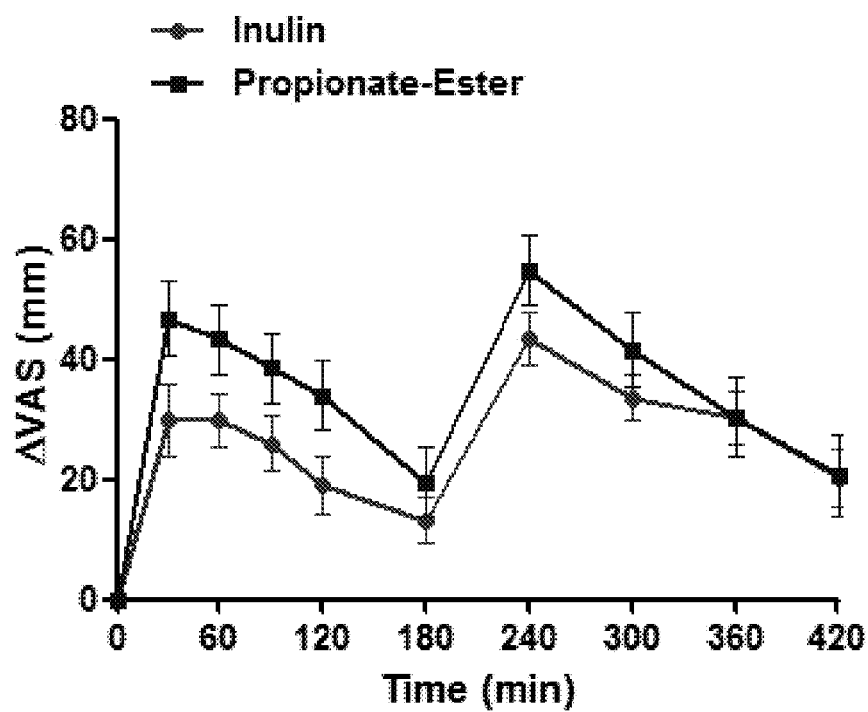
FIGS. 8(a) to (e) show visual analogue scale results for feelings of hunger, sickness, pleasantness, prospective food intake and fullness from intake of propionate inulin ester ($d_e$=0.74, 10 g) at and up to 7 hours after intake.

The Effect of Propionate Inulin Ester on Subjective Assessment of Appetite Using Validated Visual Analogue Scales in Human Volunteers Appetite was assessed throughout the entire meal study using validated visual analogue scales for feelings of hunger, sickness, pleasantness, prospective food intake and fullness. The full data are illustrated in FIGS. 8(a)-8(e). A significant increase in fullness was observed after the propionate ester supplement (8(e)) suggesting an effect on satiation (P<0.03); however, there were no significant changes in ratings of hunger, sickness, pleasantness and prospective food intake. Analysis of Fullness Ratings of 20 Subjects Following the Administration of 10 g Propionate Inulin Ester or 10 g Inulin FIG. 8(a) shows fullness at 0-420 minute post oral administration. Average iAUC was 35.0±5.2 for propionate inulin ester, vs. 26.6±2.9 for inulin, p=0.09.

Analysis of Hunger Ratings of 20 Subjects Following the Administration of 10 g Propionate Inulin Ester or 10 g Inulin FIG. 8(b) shows fullness at 0-420 minute post oral administration. Average iAUC was −25.8±4.5 for propionate inulin ester, vs. −24.3±4.7 for inulin, p=0.82

Analysis of Sickness Ratings of 20 Subjects Following the Administration of 10 g Propionate Inulin Ester or 10 g Inulin FIG. 8(c) shows fullness at 0-420 minute post oral administration. Average iAUC was −1.5±2.3 for propionate inulin ester, vs. −1.6±1.4 for inulin, p=0.95

Analysis of Pleasantness Ratings of 20 Subjects Following the Administration of 10 g Propionate Inulin Ester or 10 g Inulin FIG. 8(d) shows fullness at 0-420 minute post oral administration. Average iAUC was −25.8±3.9 for propionate inulin ester, vs. −26.6±4.6 for inulin, p=0.87

Analysis of Prospective Food Intake Ratings of 20 Subjects Following the Administration of 10 g Propionate Inulin Ester or 10 g Inulin FIG. 8(e) shows fullness at 0-420 minute post oral administration. Average iAUC was −20.9±2.7 for propionate inulin ester, vs. −19.9±3.6 for inulin, p=0.78

Effect of Propionate Inulin Ester on Release of PYY and GLP-1 in the Gut

Figure 9:
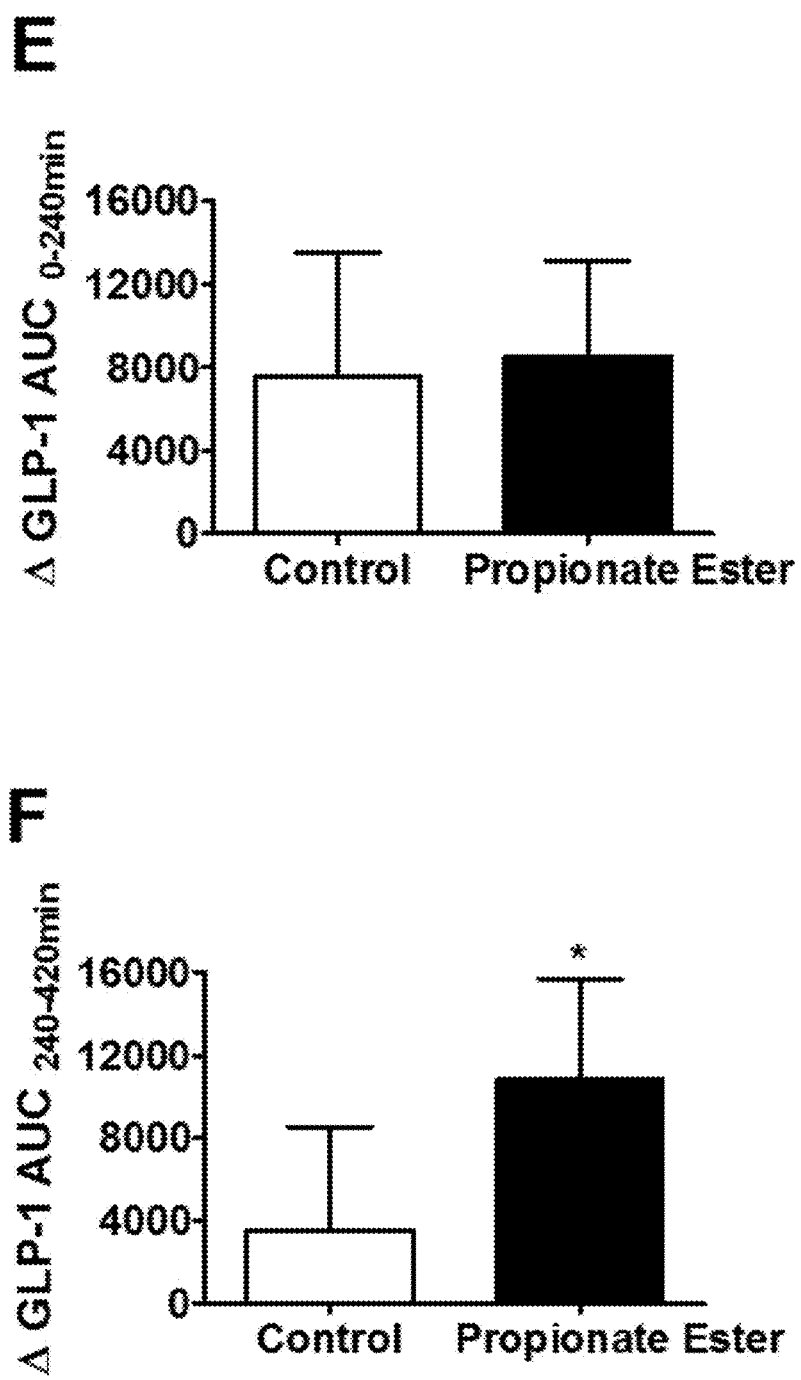
FIGS. 9(a) and (d) show the levels of gut peptides GLP-1 and PYY (pmol/L) at and up to 7 hours after intake of propionate inulin ester ($d_e$=0.74, 10 g)
FIGS. 9(b) and (e) show the plasma AUC's for these experiments between 0 and 240 min.
FIGS. 9(c) and (f) show the plasma AUC's for these experiments between 240 and 420 min.

Compared with control, propionate inulin ester significantly increased plasma PYY ($\Delta AUC_{240\text{-}420min}$429 pmol/L [95% CI, −543 to 1400] control vs. 3349 pmol/L [841 to 5857] propionate inulin ester; p<0.05) (FIGS. 9(a) and 9(c), wherein arrows indicate standardized meals) and GLP-1 levels and GLP-1($\Delta AUC_{240\text{-}420min}$3495 pmol/L [95% CI, −1567 to 8558] control vs. 10801 pmol/L [5897 to 15704] propionate inulin ester; p<0.05) between 240-420 min after ingestion (FIGS. 9(d) and 9(f)). Prior to the 240 min (the time estimated for the molecules to enter the colon) there was no significant difference in the concentration of PYY and GLP-1 between the control and the propionate inulin ester (FIGS. 9(b) and 9(e)).

Effect of Propionate Inulin Ester on Glucose Homeostasis

Figure 10:
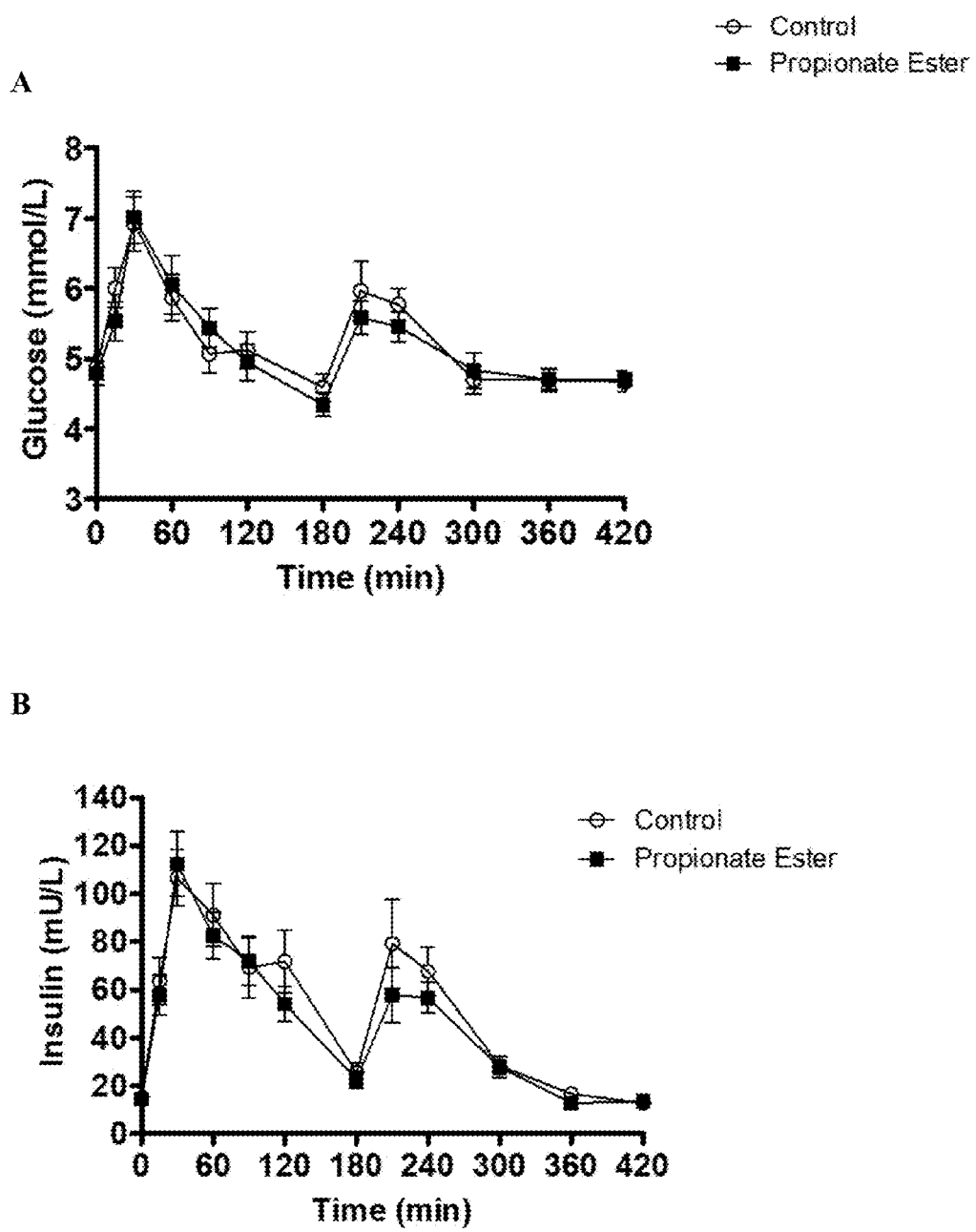
FIGS. 10(a) and (b) show the levels of glucose (mmol/L) and insulin (mU/L) at and up to 7 hours after intake of propionate inulin ester ($d_e$=0.74, 10 g).

Glucose and insulin levels were measured during the whole meal test. Neither glucose levels (average iAUC 0.32±0.16 vs. 0.28±0.12, p=0.8, FIG. 10(a)) nor insulin levels (average iAUC 28.4±2.9 vs. 32.5±4.7, p=0.27, FIG. 10(b)) were significantly different between the propionate inulin ester and inulin supplement.

Example 7

Effect of Free Propionate on PYY and GLP-1 Release Form Human L-Cell In Vitro

Materials and Methods

Isolation of Human Colonic Cells

Colonic biopsies were obtained from patients undergoing diagnostic colonoscopy at Hammersmith Hospital. All subjects provided informed, written consent prior to the study, approval for which was granted by the Hammersmith and Queen Charlotte's Research Ethics Committee.

The colonic tissue was digested as described previously (Reimann et al. 2008) with minor modifications. Briefly, the tissue was digested with 0.4 mg/ml collagenase XI (Sigma, UK) in Dulbecco's Modified Eagle Medium (DMEM) at 37° C. Resulting cell suspensions were centrifuged for 5 minutes at 500 g and the pellets were re-suspended in DMEM (supplemented with 10% FCS and 1% penicillin/streptomycin). The digestion process was repeated three-four times and the combined cell suspensions were plated onto 24-well, 1% Matrigel-coated plates and incubated at 37° C. in an atmosphere of 5% $CO_2$.

In Vitro Gut Hormone Secretion Experiments

Secretion experiments were carried out 18-24 hours after plating of the colonic cells. The cells were washed twice with secretion buffer (4.5 mM KCl, 138 mM NaCl, 4.2 mM $NaHCO_3$, 1.2 mM $NaH_2PO_4$, 2.6 mM $CaCl_2$, 1.2 mM $MgCl_2$ and 10 mM HEPES, adjusted to pH 7.4 with NaOH) containing 0.1% BSA. Cells were incubated with sodium propionate (Sigma, UK) for 4 hours at 37° C. in an atmosphere of 5% $CO_2$. Following incubation, cell supernatants were centrifuged to remove cell debris and the plates were treated with lysis buffer and freeze-thawed. Gut hormone secretion was expressed as percentage hormone release, calculated for each well, and normalised to basal secretion. Cell health was confirmed using a CytoScan™ lactate dehydrogenase assay (G-Biosciences).

Results:

Propionate significantly stimulated PYY secretion from human colonic cells, with concentrations of 200 and 400 mmol/L inducing 1.8- and 3.0-fold rises above basal secretion, respectively (P<0.05 and P<0.001). Propionate also increased GLP-1 secretion, with 200 and 400 mmol/L inducing 1.6- and 2.4-fold (P<0.001) increases in GLP-1 release, respectively (see FIG. 11).

Example 8a

Further Purification Method

Methods and Materials

A 3-day dialysis in dialysis tubing (Spectra/Por 6, 1000 MWCO, Spectrum Europe B.V., Breda, Netherlands) was carried out on propionate inulin ester as prepared in example 1 ($d_e$=0.74).

Results

Dialysis resulted in complete removal of the salt. Loss of ester yield (about 50%) resulted, but without compromising ester quality. In addition, the amount of free propionate was reduced by dialysis to <1% of the total propionate available after full de-esterification.

Example 8b

Palatability Study

Materials and Methods 10 g of propionate inulin ester as prepared in example 1 ($d_e$=0.74) and 10 g of propionate inulin ester as prepared in example 1 and purified as in example 8a ($d_e$=0.74) were dissolved in water and in fruit juice. A palatability study was carried out using validated visual analogue scales for feelings of hunger, sickness, pleasantness, prospective food intake and fullness.

Results

The ester purified by dialysis, with no salt and less propionate the ester purified by charcoal columns alone, was more palatable for human consumption. The purification by dialysis resulted in a product that was almost tasteless when dissolved in water and undetectable when dissolved in fruit juice. The ester purified by charcoal columns alone has a bitter taste when dissolved in water and slightly bitter taste when dissolved in fruit juice.

Example 9

Long Term Food Supplementation Investigation in Human Subjects

Materials and Methods:

Propionate Inulin Ester

Propionate inulin ester was produced with a degree of esterification, $d_e$=0.74±0.02 (n=12) and a level of free propionate of 2.57±0.26% (n=12) of the total propionate available from the molecule. 97% of recovered propionate was chemically bound to the inulin polymer.

Study Subjects

Figure 12:
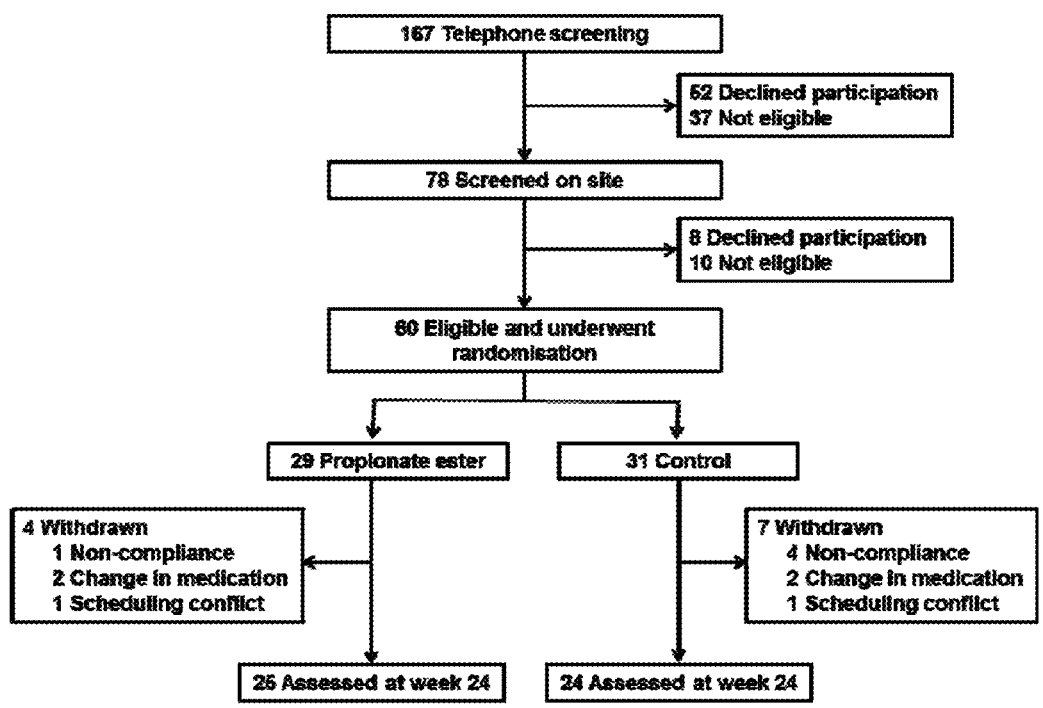
FIG. 12 shows process for recruitment and retention of subjects in the long term food supplementation investigation in human subjects.

Healthy men and women aged 40-65 years, with a BMI of 25-40 kg/m² were recruited from the general public. Potential subjects were excluded if they had clinically significant illnesses (including type 1 or type 2 diabetes), were taking medication known to affect appetite and/or body weight, a weight loss of 3 kg or greater in the preceding two months, smoking, substance abuse, psychiatric illness, restrained eating (Dutch eating behavior questionnaire: male score >2.25; female score >2.80), and any abnormalities detected on physical examination, electrocardiography, or screening blood tests (measurement of complete blood count, electrolytes, fasting glucose, thyroid function and liver function). Women were ineligible if they were pregnant or breastfeeding. From an initial 167 persons who responded to letters of invitation, the final sample after screening comprised 60 persons. The screening process is shown in FIG. 12. All subjects provided informed, written consent prior to the clinical trial (Registration No: NCT00750438), which was approved by the Hammersmith and Queen Charlotte's Research Ethics Committee (08/H0707/99). The study was carried out in accordance with the Declaration of Helsinki.

(a) Food Supplementation Investigation

The study was conducted in a randomized, double-blind, placebo-controlled, parallel design. Two-day study visits were required at baseline (week 0) and after 24 weeks of dietary supplementation. On the day prior to each study visit, subjects were asked to consume a standard evening meal, fast overnight from 22:00 and to avoid strenuous physical activity and alcohol. All study visits commenced between 08:00 and 09:00. After all baseline measurements had been taken, subjects were randomly assigned to either the 10 g/day propionate inulin ester group, or the 10 g/day inulin control group. The dietary supplement was supplied to subjects in ready-to-use sachets and they were instructed to mix the contents into their normal diet once a day during the 24 week treatment period. All subjects were instructed to maintain their usual dietary and activity habits during the intervention period. Regular communication between subjects and study investigators ensured good compliance. After 8 and 16 weeks of the intervention period, subjects were invited to attend follow-up visits to record body weight and monitor compliance and gastrointestinal side-effects. After 24 weeks, measurements taken at baseline were repeated. Subjects returned all their used and unused sachets to estimate compliance. Symptom diary was also collected over the period of the study.

(b) Food Intake and Glucose Homeostatis

At study visits, a cannula was inserted into an antecubital vein and baseline blood samples were collected at −10 and 0 min to assess plasma concentrations of glucose, insulin, PYY and GLP-1. Following the 0 min sample, subjects were served a standardized breakfast (398 kcal; 71.2 g CHO, 7.9 g fat, 10.3 g protein). At week 24, the breakfast also contained 10 g of propionate inulin ester or 10 g inulin control depending on treatment group. Postprandial blood samples were taken at 15, 30, 60, 90, 120, 180, 240 and 300 min and collected into heparin-coated tubes containing 0.2 ml of aprotinin (Bayer, UK). GLP-1- and PYY-like immunoreactivity was measured using specific and sensitive in-house radioimmunoassays. Insulin-like immunoreactivity was measured using an ultra-sensitive human insulin radioimmunoassay (Millipore) and plasma glucose was measured using an Abbott Architect ci8200 analyser (Abbott Diagnostics, USA). At 300 min subjects were offered a buffet lunch with food served in excess and subjects were asked to eat until they were comfortably full. The amount of food was quantified and energy intake calculated. Subjective hunger, satiety, and nausea were monitored with the use of 100 mm visual analog scales (VAS). Subjects were asked to complete the VAS before each blood sample. In addition, breath $H_2$ was measured at 0, 60, 120, 180, 240 and 300 min (Bedfont Scientific, Kent UK) in a subset of each group (9 in the propionate ester group, 8 in the inulin control group).

(c) Body Composition

Body composition was assessed using magnetic resonance imaging (MRI) and spectroscopy (MRS). MRI and MRS data could not be collected in 19 subjects, due to metal implants (n=8), claustrophobia (n=9) and technical issues with the scanner (n=2). Body weight was measured in all subjects to the nearest 0.1 kg (TBF-300, Tanita) and taken while subjects were wearing light clothing.

(d) Risk Factors for Cardiovascular Disease and Diabetes

A fasting blood sample was collected and analysed for levels of triglycerides, total cholesterol, low-density lipoprotein (LDL) cholesterol, high-density lipoprotein (HDL) cholesterol, glycosylated haemoglobin (HbA1c), and liver function tests (alanine transaminase, alkaline phosphatase, aspartate transaminase). Blood pressure and pulse were also measured after subjects had been in a supine position for at least 15 minutes.

(e) Fluorescent In Situ Hybridisation to Assess Gut Microbial Changes to Propionate Inulin Ester and Inulin Control Faecal samples were obtained from three healthy human volunteers (one female and two males; age 30-50 years; BMI 25-31). Volunteers were excluded if they suffered from any gastrointestinal disorder (e.g. ulcerative colitis, Crohn's disease, irritable bowel syndrome, peptic ulcers and cancer) and/or had taken antibiotics in the six months preceding sample donation. Samples were kept under anaerobic conditions (10% H2, 10% CO2 and 80% N2) and used within a maximum of 30 minutes following collection. Samples were diluted 1/10 w/w in anaerobic PBS (0.1 mol/l phosphate buffer solution, pH 7.4) and homogenised in a stomacher (Stomacher 400, Seward, West Sussex, UK) for 2 minutes at normal speed.

Sterile batch culture fermenters (150 ml working volume) were set up in parallel and aseptically filled with 135 ml pre-reduced, sterile basal culture medium (peptone water 2 g/l (Oxoid), yeast extract 2 g/l (Oxoid, Basingstoke, UK), NaCl 0.1 g/l, $K_2HPO_4$ 0.04 g/l, $KH_2PO_4$ 0.04 g/l, $MgSO_4.7H2O$ 0.01 g/l, $CaCl_2.6H2O$ 0.01, $NaHCO_3$ 2 g/l, Tween 80 2 ml (BDH, Poole, UK), haemin 0.05 g/l, vitamin $K_1$ 10 cysteine.HCl 0.5 g/l, bile salts 0.5 g/l). The fermenters were gassed overnight with $O_2$ free $N_2$. Propionate inulin ester and inulin control substrates (1/10 w/v) were added to their respective fermenters just prior to the addition of the faecal slurry. A substrate-free vessel was set up for each volunteer as the negative control. Cultures were continuously stirred and kept at 37° C. by means of a circulating water bath. Culture pH was kept between 9.7 and 6.9 using automated pH controllers (Fermac 260, Electrolab, Tewkesbury, UK). Each vessel was inoculated with 15 ml fresh fecal slurry (1/10 w/w). Batch fermentations were ran for 48 h and 6 ml samples were obtained from each vessel at 0, 10, 24, 34 and 48 h for fluorescent in situ hybridisation (FISH) analysis. Three replicate fermentations were set up, each inoculated with one of three different human fecal samples.

Fluorescent in situ hybridization targeting *Bifidobacterium* spp (Bif164), *Bacteroides/Prevotella* (Bac303), *Lactobacillus/Enterococcus* (Erec482), *Clostridium histolyticum* (Chis150), *Atopobium* cluster (Ato291) and *Eubaterium rectale/Clostridium coccoides* (Erec482), was used as described by Sarbini et al (2011). Cells were visualized using fluorescent microscopy (Eclipse 400, Nikon, Surrey, UK) using the Fluor 100 lens. For each sample, 15 different fields of view were enumerated. Univariate analysis of variance (ANOVA) and Tukey's post hoc test were used to determine the significant differences of substrates used on bacterial group populations.

Statistical Analysis

The sample size for the acute food intake study was based on a power calculation, assuming a decrease of 15% in energy intake with a standard deviation of 20% ($\alpha=0.05$, power=0.85), resulting in an estimated required sample size of 20 per group. Data from the acute supplementation study was used to estimate the required sample size for the long term investigation. The sample size was calculated assuming that the SD of the difference in energy intake at week 24 would be 250 kcal. 52 individuals (26 in each group) would provide 80% confidence ($\alpha=0.05$) to detect a 200 kcal difference in food intake between the propionate inulin ester and inulin control treatment groups. Data was analysed from the 49 subjects that completed the 24 week intervention (per-protocol analysis; FIG. 13). 11 subjects (18%) did not complete the 24 week intervention and there were no significant differences in attrition between the two groups, as shown in FIG. 12. Baseline and post-intervention body composition data was collected from 17 subjects in the propionate inulin ester group and 15 subjects in the control group. For comparison of continuous variables, the change from baseline at 24 weeks was calculated in each subject and compared means within group using paired t-tests and compared the mean change between groups using unpaired t-tests. Chi-square tests were performed to compare percentages of subjects in each group who gained ≥3% and ≥5% of their initial weight. One-way ANOVA was performed to determine differences in in vitro secreted gut hormone levels. Differences in energy intake and area under the curve (AUC) for plasma hormone levels between trials were assessed using Paired Student's t test. Two-way (trial×time) repeated measures ANOVA was performed to determine differences in plasma hormone levels, VAS and breath hydrogen. Significant effects were followed up by post hoc comparisons. P values<0.05 were considered statistically significant. Data are presented as means±SEM or ±95% Confidence Interval [CI].

Results

Weight Loss and Body Composition

After 24 weeks of dietary supplementation, the propionate inulin ester group had lost a mean body weight of 1.02±0.57 kg (p=0.062), whereas the control group had gained 0.38±0.69 kg (p=0.558). The difference in weight loss between groups was not significantly different over the 24 week period (FIG. 14(a); p=0.097). The weight loss within the propionate inulin ester group from weeks 16 to 24 was significant (0.81±0.26 kg; p=0.002). We found a weight gain in excess of normal weight maintenance (≥3% baseline weight) occurred in 1 of 25 subjects following propionate inulin ester treatment (4%), as compared with 6 of 24 subjects (25%) in the control group (FIG. 14(b); P=0.036). Furthermore, none of the subjects had substantial weight gain (≥5% baseline weight) in the propionate inulin ester group compared with 4 of 24 (17%) following control treatment (FIG. 14(b); P=0.033).

Following the intervention period, there was no significant change in total adipose tissue content between groups, however, following treatment the change in the distribution of internal fat in the abdominal area (expressed as a percentage of total adipose tissue content) was significantly lower in the propionate inulin ester group compared with control supplementation (FIG. 15; p=0.040). Furthermore, internal adipose tissue was significantly increased within the control group (p=0.049) and the ratio of internal adipose tissue:subcutaneous adipose tissue was significantly increased (p=0.002). Intrahepatocellular lipid (IHCL) was significantly reduced within the propionate inulin ester treatment group (p=0.038), but the changes in IHCL, soleus and tibialis intramyocellular lipid (IMCL) were not significantly different between intervention groups. In vitro analysis suggests that the protective effects of the propionate inulin ester on weight gain and fat distribution are not due to changes in gut bacterial populations compared with control (see "Gut Microbial Changes to Propionate inulin ester and Control" results below and FIG. 16).

Subject Compliance and Adverse Events

Compliance for the propionate inulin ester group and inulin group was similar over the total 24 week period. Mean compliance, based on number of unopened sachets at end of 24 week study, was 95±7% for propionate inulin ester group and 94±7% for inulin group.

Compliance over weeks 0 to 8, 9 to 16 and 17 to 24 for the propionate inulin ester group was as follows: weeks 0 to 8: 96±9%; weeks 9 to 16: 96±6%; and weeks 17 to 24: 93±9%. Compliance over weeks 0 to 8, 9 to 16 and 17 to 24 for the inulin group was as follows: weeks 0 to 8: 97±3%; weeks 9 to 16: 94±10%; and weeks 17 to 24: 92±13%.

Figure 17:
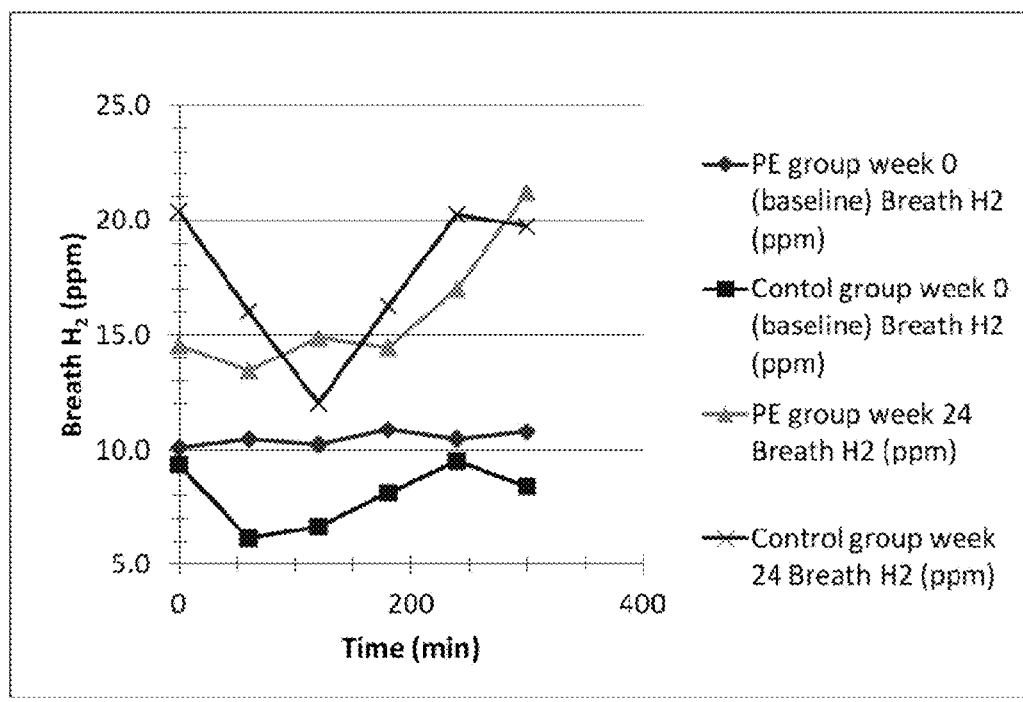
FIG. 17 shows mean level of breath hydrogen (ppm) following consumption of standard breakfast at baseline (0 week) and following consumption of standard breakfast including 10 g propionate inulin ester ($d_e$=0.74) (PE group) or 10 g inulin (Control group) following 24 weeks of propionate inulin ester and inulin control supplementation (week 24).

There was a significant increase from baseline (control 9±3 v 19.1±7 p<0.05 propionate inulin ester 10±4 v 14±4 p<0.01) to 24 weeks in fasting and area under curve (control 2355±800 v 5000±1480 p<0.05 propionate inulin ester 3146±1137 v 4660±1268 p<0.05) for breath hydrogen in the both groups suggesting the consumption of inulin or propionate inulin ester (see FIG. 17).

The side effect profile was greater in the inulin control group with significant increase in bloating and flatulence at week 24 that was not seen in the propionate inulin ester group.

Food Intake and Gut Hormone Release

Figure 18:
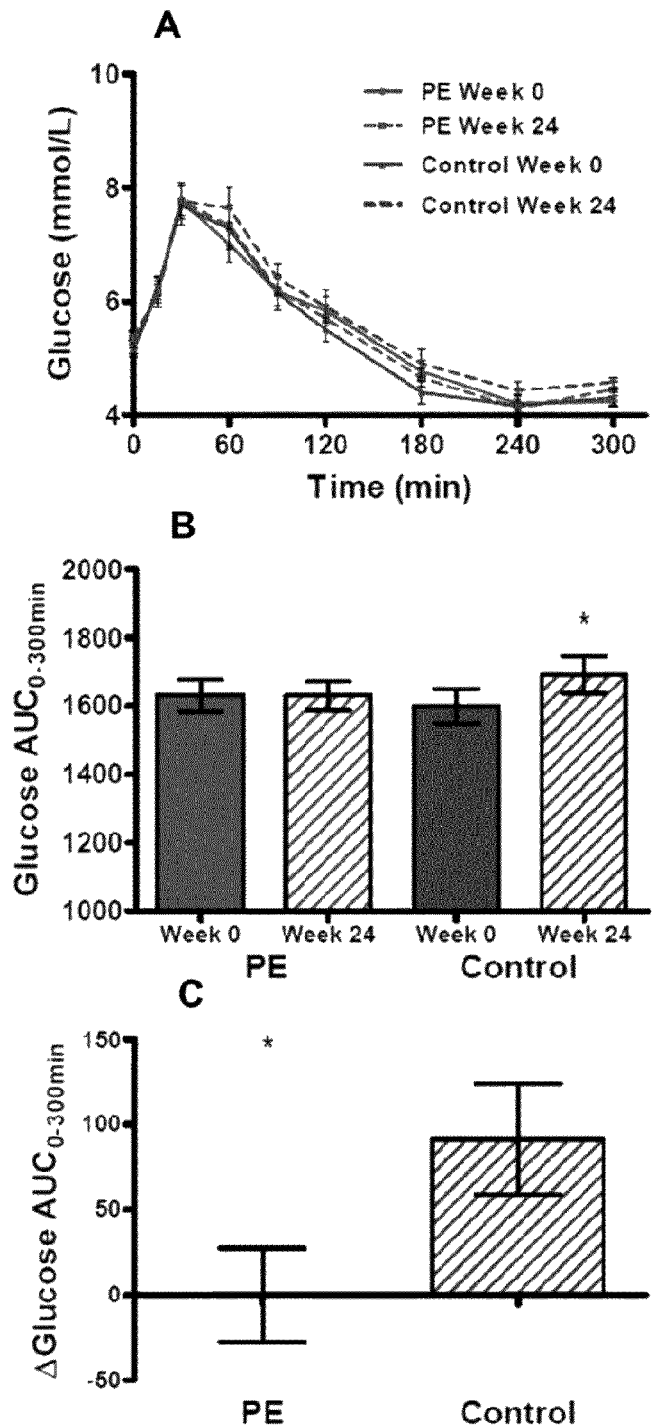
FIG. 18(a) shows postprandial glucose response (mmol/L) at baseline (week 0) and at week 24 following 24 weeks of supplementation with propionate inulin ester ($d_e$=0.74) and inulin control.
FIG. 18(b) shows glucose plasma glucose AUC's at baseline (week 0) and at week 24 following 24 weeks of supplementation with propionate inulin ester ($d_e$=0.74) and inulin control.
FIG. 18(c) shows the change from baseline (week 0) glucose plasma AUC and at week 24 following 24 weeks of supplementation with propionate inulin ester ($d_e$=0.74) and inulin control.
Figure 19:
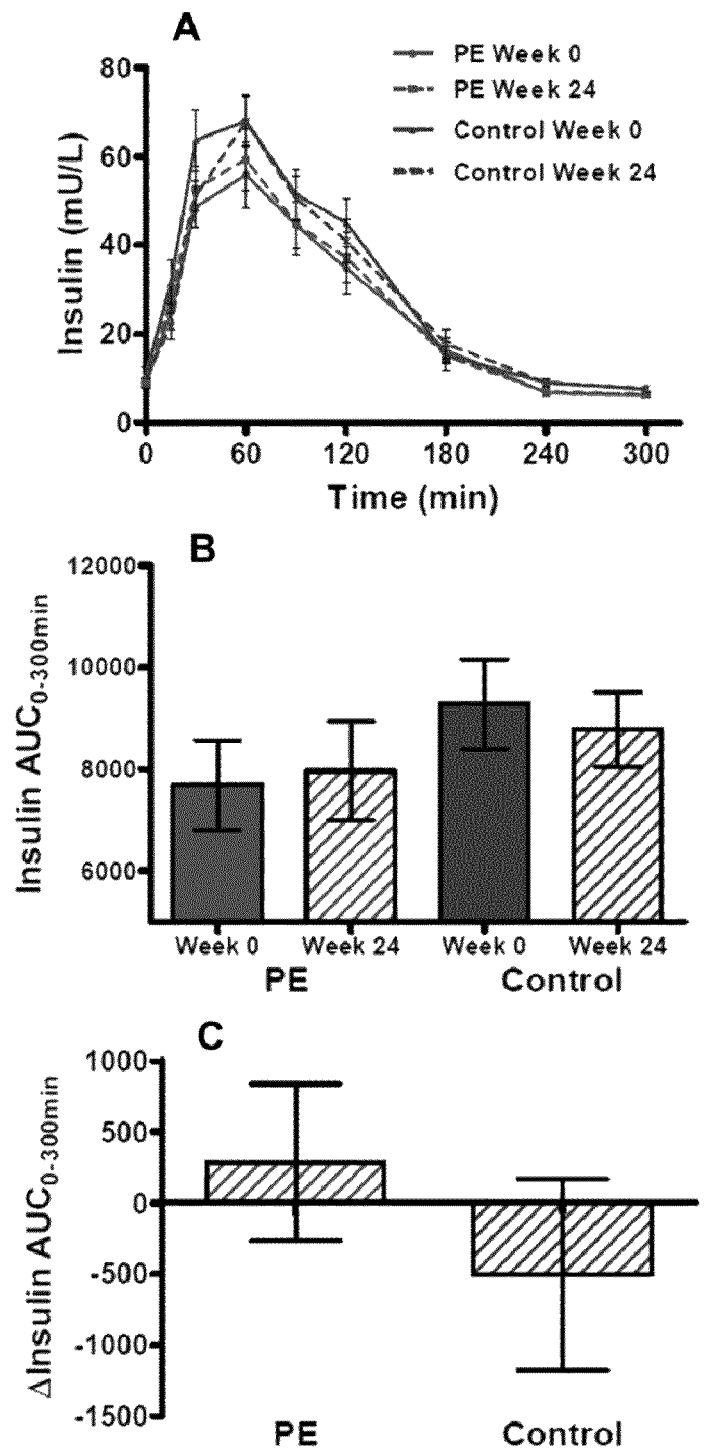
FIG. 19(a) shows postprandial insulin response (mU/L) at baseline (week 0) and at week 24 following 24 weeks of supplementation with propionate inulin ester ($d_e$=0.74) and inulin control.
FIG. 19(b) shows plasma insulin AUC's at baseline (week 0) and at week 24 following 24 weeks of supplementation with propionate inulin ester ($d_e$=0.74) and inulin control.
FIG. 19(c) shows the change from baseline (week 0) insulin plasma AUC and at week 24 following 24 weeks of supplementation with propionate inulin ester ($d_e$=0.74) and inulin control.

Propionate inulin ester treatment reduced food intake by 8.7% from 836±56 kcal to 763±54 kcal (p=0.100). Control supplementation reduced food intake from 678±69 kcal to 651±64 kcal (p=0.197), a mean reduction of 4.0%. The change in food intake was not statistically significant between groups (p=0.416). There was no difference in plasma PYY (ΔAUC0-300 min 1148±712 pmol/L to 907±556 pmol/L; p=0.756) or GLP-1 release (ΔAUC0-300 min 4232±1070 pmol/L to 3216±847 pmol/L; p=0.447) during the postprandial period following long-term propionate inulin ester supplementation. Plasma PYY (ΔAUC0-300 min 962±869 pmol/L to 656±880 pmol/L; p=0.817) and GLP-1(ΔAUC0-300 min 3441±843 pmol/L to 2278±1000 pmol/L; p=0.334) were also unaffected by control treatment. The change in PYY (FIG. 14(c); p=0.965) and GLP-1 (See FIG. 14(d); p=0.993) release were not significantly different between treatment groups Glucose Homeostatis The change in postprandial glucose response to the standardized breakfast at week 24 was significantly different between groups (FIG. 18; p=0.037). Glycemic response was significantly greater following control supplementation (AUC0-300 min 1600±51 pmol/L to 1691±54 pmol/L; p=0.010) and unchanged following propionate inulin ester treatment (AUC0-300 min 1630±50 pmol/L to 1630±42 pmol/L; p=0.993), in keeping with the differences in weight gain and body fat distribution experienced within the groups. Insulin response was not significantly different following propionate inulin ester (AUC0-300 min 7684±881 µU/mL to 7969±971 µU/mL; p=0.612) or control treatment (AUC0-300 min 9285±882 µU/mL to 8781±731 µU/mL; p=0.464) and the change in insulin response was not significantly different between groups (FIG. 19; p=0.372).

Risk Factors for Cardiovascular Disease and Diabetes

Figure 14:
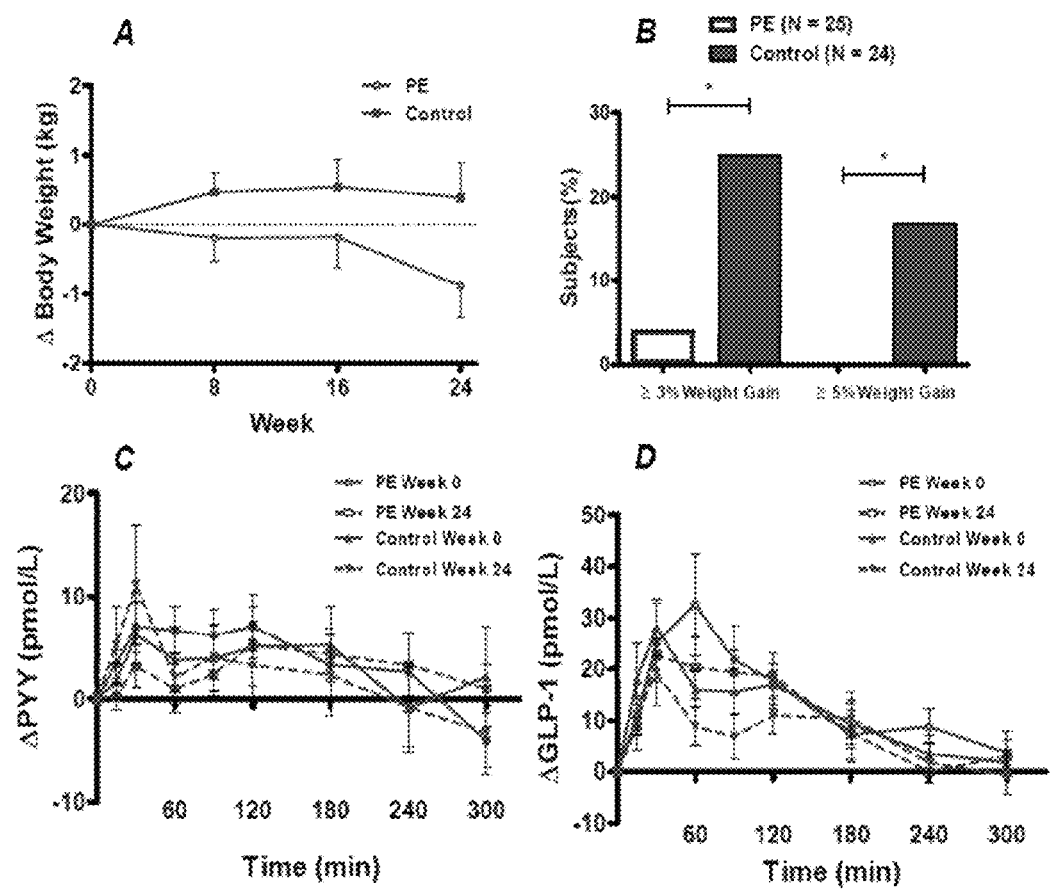
FIG. 14(a) shows effects of 24 weeks propionate inulin ester ($d_e$=0.74) and inulin control supplementation on body weight.
FIG. 14(b) shows the proportion of subjects who gained 3% or more and 5% or more of their baseline weight at end of 24 weeks propionate inulin ester ($d_e$=0.74) and inulin control supplementation.
FIGS. 14(c) and (d) show the levels of gut peptides GLP-1 and PYY (pmol/L) at baseline (week 0) and following 24 weeks of propionate inulin ester ($d_e$=0.74) and inulin control supplementation (week 24).

Propionate inulin ester supplementation significantly reduced total cholesterol (p<0.001), LDL (p<0.001), HDL (p=0.004), alanine transaminase (p=0.015), alkaline phosphatase (p<0.001) and aspartate transaminase (p=0.007). Total cholesterol (p=0.014), HDL (p<0.001), alanine transaminase (p<0.001) and alkaline phosphatase (p<0.001) were significantly reduced from baseline values in the control group. Propionate inulin ester and control treatments had no significant effect on fasting glucose, insulin, HbA1c and triglyceride concentrations (FIG. 14).

Gut Microbial Changes to Propionate Inulin Ester and Control

Inulin control significantly increased Bif164 labelled cells at all time points compared to baseline. Bif164 levels with control were significantly higher compared to the concentrations in propionate inulin ester cultures throughout fermentation. Both propionate inulin ester and inulin control mediated significant increases in Bac303 labelled cells at all sampling points compared to baseline levels. Ato291 labelled cells increased significantly with both test substrates between 10 and 34 h batch culture fermentation compared to baseline concentrations. No other significant changes were seen in any of the groups targeted or total bacteria levels. It appears that propionate inulin ester is fermentable by *Bacteroides* and *Atopobium* but is not metabolised by *Bifidobacterium* spp. FIG. 16 shows these results.

The invention claimed is:

1. A method of treatment comprising administering to a subject a propionate inulin ester or a pharmaceutical composition comprising the propionate inulin ester, wherein said treatment comprises reducing appetite, reducing food intake, reducing calorie intake, reducing or preventing weight gain, treating obesity, or treating diabetes in the subject in need thereof.

2. The method of claim 1, wherein said treatment is the treatment of obesity or diabetes.

3. The method of claim 1, wherein degree of substitution of the propionate inulin ester is between 0.2 and 1.

4. The method of claim 1, wherein degree of substitution of the propionate inulin ester is between 0.55 and 1.

5. The method of claim 1, wherein the propionate inulin ester is administered in an amount providing from about 0.1 mg of propionate inulin ester per kilogram (kg) body weight to about 500 mg per kg body weight.

6. The method of claim 1, wherein the propionate inulin ester is administered orally.

7. The method of claim 1, wherein the propionate inulin ester is added to food or used as a food additive.

8. The method of claim 1, wherein the subject is overweight.

9. The method of claim 1, wherein the subject is diabetic.

10. The method of claim 1, wherein the propionate inulin ester is administered to a subject in a daily dose of between 5 g and 20 g.

11. The method of claim 1, wherein the treatment is use of the propionate inulin ester for the reduction of appetite, food intake or calorie intake, or for reducing or preventing weight gain, and the subject is with a normal BMI.

12. The method of claim 1, wherein the propionate inulin ester is administered with a therapeutically effective amount of another agent selected from an additional appetite suppressant, an additional food-intake-reducing agent, a plasma glucose-lowering agent, or plasma lipid-altering agent, or any combination thereof.

13. A functional food containing propionate inulin ester.

14. A pharmaceutical composition comprising
a propionate inulin ester, and
one or more pharmaceutically acceptable solid excipients.

15. The pharmaceutical composition of claim 14, further comprising an additional appetite suppressant.

16. A kit comprising:
a propionate inulin ester, and
an additional appetite suppressant,
the two (or more) components being for co-administration simultaneously, separately or sequentially.

17. A propionate inulin ester with a degree of substitution between 0.55 and 1.

18. A method for preparing the propionate inulin ester of claim 17, comprising dissolving inulin in water to give a concentration of between 1 and 2 moles of fructose equivalents per liter, lowering the temperature of the solution to between 10 and 20° C., adding propionic anhydride and an aqueous alkali metal base with a concentration between 20 and 100% w/v to the solution while keeping the temperature of the solution between 10 and 20° C. and the pH of the solution between pH 8 and 8.5; to give the desired degree of substitution the number of moles of propionic anhydride added to the inulin is calculated as: number of moles of fructose unit equivalents in solution×target degree of substitution×1.25.

19. A method of purifying the propionate inulin ester of claim 17, comprising dissolution of propionate inulin ester in water, adjusting the pH of the solution to pH 2 with concentrated strong acid, passing the solution though an activated charcoal column washed and conditioned with 0.2 M strong acid, recovering the solution from the column, adjusting to pH 2 with concentrated strong acid, passing the solution through though a second activated charcoal column washed and conditioned with 0.2 M strong acid, recovering the solution from the column, adjusting to pH 2 with concentrated strong acid and spray drying.

20. The method of claim 1, wherein said treatment is the prevention of obesity or diabetes.

21. A functional food as claimed in claim 13 containing a therapeutically effective amount of the propionate inulin ester.

22. A pharmaceutical composition as claimed in claim 14 containing a therapeutically effective amount of the propionate inulin ester.

* * * * *